United States Patent
Landfester et al.

(10) Patent No.: US 10,739,334 B2
(45) Date of Patent: Aug. 11, 2020

(54) CAPSULE SUITABLE FOR NON-INVASIVE SIMULTANEOUS OXYGEN CONTENT AND TEMPERATURE SENSING IN A LIVING OBJECT

(71) Applicant: MAX-PLANCK-GESELLSCHAFT ZUR FÖRDERUNG DER WISSENSCHAFTEN E.V., Munich (DE)

(72) Inventors: Katharina Landfester, Mainz (DE); Yury Avlasevich, Heidesheim (DE); Dzmitry Busko, Mainz (DE); Frederik Wurm, Wiesbaden (DE); Stanislav Balouchev, Mainz (DE)

(73) Assignee: MAX-PLANCK-GESELLSCHAFT ZUR FORDERUNG DER WISSENSCHAFTEN E.V., Munich (DE)

( * ) Notice: Subject to any disclaimer, the term of this patent is extended or adjusted under 35 U.S.C. 154(b) by 0 days.

(21) Appl. No.: 15/560,210

(22) PCT Filed: Mar. 4, 2016

(86) PCT No.: PCT/EP2016/054605
§ 371 (c)(1),
(2) Date: Sep. 21, 2017

(87) PCT Pub. No.: WO2016/150677
PCT Pub. Date: Sep. 29, 2016

(65) Prior Publication Data
US 2018/0106785 A1    Apr. 19, 2018

(30) Foreign Application Priority Data
Mar. 24, 2015  (EP) .................................. 15160620

(51) Int. Cl.
*G01N 33/50* (2006.01)
*C09K 11/06* (2006.01)
(Continued)

(52) U.S. Cl.
CPC .......... *G01N 33/5091* (2013.01); *A61B 5/01* (2013.01); *A61B 5/14542* (2013.01);
(Continued)

(58) Field of Classification Search
CPC ............ C09K 11/06; C09K 2211/1011; C09K 2211/1018; C09K 2211/1029;
(Continued)

(56) References Cited

U.S. PATENT DOCUMENTS

| | | | |
|---|---|---|---|
| 2010/0301285 A1 | 12/2010 | Miteva et al. | |
| 2011/0013263 A1 | 1/2011 | Miteva et al. | |
| 2016/0222286 A1* | 8/2016 | Landfester | C09K 11/06 |

FOREIGN PATENT DOCUMENTS

WO    2012052068 A1    4/2012

OTHER PUBLICATIONS

Bradley B. Collier et al., Microparticle ratiometric oxygen sensors utilizing near-infrared emitting quantun dots, Analyst, 2011, pp. 962-967, vol. 136, The Royal Society of Chemistry.
(Continued)

*Primary Examiner* — Kortney L. Klinkel
(74) *Attorney, Agent, or Firm* — Cantor Colburn LLP

(57) ABSTRACT

A capsule suitable for oxygen and temperature sensing contains:
i) at least one first sensitizer compound being capable of energy transfer to triplet oxygen,
ii) at least one compound being capable of reacting with and inactivating singlet oxygen,
iii) at least one second sensitizer compound being capable of absorbing radiation at a second frequency $v_2$ and of emitting light at a fourth frequency $v_4$,
(Continued)

Figure 1:
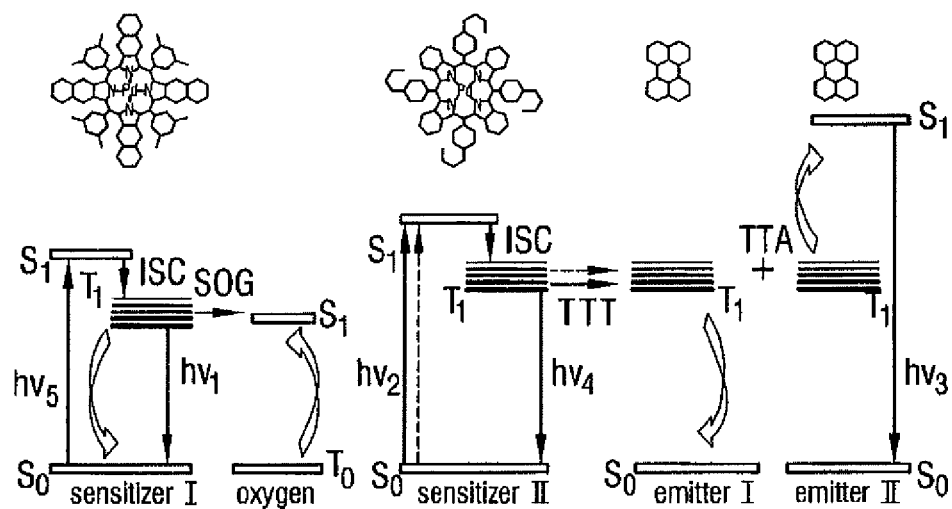

iv) at least one emitter compound, wherein the at least one second sensitizer compound is capable of transferring energy to the at least one emitter compound and wherein the at least one emitter compound, after obtaining energy transferred from the at least one second sensitizer compound, is capable of emitting light at a third frequency $v_3$, wherein the following equation is fulfilled: $v_3 > v_2$,
wherein the upper energy limit of the first triplet energy band of the first sensitizer compound is lower than the lower energy limit of the second triplet energy band of the second sensitizer compound and lower than the lower energy limit of the third triplet energy band of the emitter compound, and wherein the third triplet band of the emitter compound at least partially overlaps with the second triplet energy band of the second sensitizer compound.

19 Claims, 3 Drawing Sheets

(51) Int. Cl.
　　*A61B 5/01*　　　(2006.01)
　　*A61B 5/145*　　 (2006.01)
　　*A61K 49/00*　　 (2006.01)
　　*G01N 31/22*　　 (2006.01)

(52) U.S. Cl.
　　CPC .......... *A61K 49/0015* (2013.01); *C09K 11/06* (2013.01); *C09K 2211/1011* (2013.01); *C09K 2211/1018* (2013.01); *C09K 2211/1029* (2013.01); *C09K 2211/185* (2013.01); *G01N 31/225* (2013.01)

(58) Field of Classification Search
　　CPC .......... C09K 2211/185; G01N 31/225; G01N 33/5091; A61B 5/01; A61B 5/14542; A61K 49/0015
　　See application file for complete search history.

(56) References Cited

OTHER PUBLICATIONS

Dayoung Song et al., Ratiometric Fluorescent Probes for Detection of Intracellular Singlet Oxygen, Organic Letters, 2013, pp. 3582-3585, vol. 15, No. 14, American Chemical Society.
European Search Report from the European Patent Office for related EP Application No. 15160620.9, dated Sep. 9, 2015; 6 pages.
F. Li et al., Fluorescent/phosphorescent dual-emissive conjugated ploymer dots for hypoxia bioimaging, Chemical Science, 2012, pp. 1-6. vol. 00, The Royal Science of Chemistry.
International Preliminary Report on Patentability; International Application No. PCT/EP2016/054605; dated Sep. 26, 2017, 7 pages.
International Search Report; International Application No. PCT/EP2016/054605; dated Jun. 1, 2016; 5 pages.
Kyle B. Guice et al., Nanoscale internally referenced oxygen sensors produced from self-assembled nanofilms on fluorescent nanoparticles, Journal of Biomedical Optics, Nov./Dec. 2005, pp. 064031-1 to 064031-10, vol. 10(6).
Written Opinion of International Searching Authority; International Application No. PCT/EP2016/054605; dated Jun. 1, 2016; 6 pages.
Xiao-Hui Wang et al., Biocompatible fluorescent core-shell nanoparticles for ratiometric oxygen sensing, Journal of Materials Chemistry, 2012, pp. 16066-16071, vol. 22, The Royal Society of Chemistry.

\* cited by examiner

CAPSULE SUITABLE FOR NON-INVASIVE SIMULTANEOUS OXYGEN CONTENT AND TEMPERATURE SENSING IN A LIVING OBJECT

CROSS-REFERENCES TO RELATED APPLICATIONS

This patent application is a 371 of International Application No. PCT/EP2016/054605, filed Mar. 4, 2016 which claims the priority of European Application No. 15160620.9, filed Mar. 24, 2015 each of which are incorporated herein by reference in their entirety.

The present invention relates to a capsule, which allows the non-invasive and intracellular determination of the oxygen content and temperature in a living object with a single sensor.

Sensors for detecting the oxygen content and temperature in a living object are important to evaluate the health condition of a living object. All biochemical reactions, which are responsible for cellular functions, occur at particular locations within a cell, wherein the intracellular oxygen concentration as well as the local temperature within a cell are tightly regulated and maintained within narrow physiological limits. Thus, variations of the oxygen content and/or temperature in a cell are a strong indicator for a disease. Accordingly, the determination of the oxygen content and temperature in a cell allows to draw conclusions about the health condition of the living object. For example, hypoxia, which is a condition in which at least a part of the body is deprived of oxygen supply, can be easily determined by measuring the oxygen content in different cells of an organism. On account of the fact that hypoxia in turn is closely related to several diseases, such as tumors and retinal diseases, the measurement of the oxygen content in a living organism is an important diagnosis tool. The same is valid for the measurement of the temperature in different cells of a living organism. Accordingly, the non-invasive intracellular thermometry and oximetry can be used to probe many functional characteristics of biological specimens, such as their physiological behavior under various conditions, metabolic parameters and responses to drug treatment or other stimuli.

Various techniques for intracellularly measuring the local oxygen concentration and the local temperature distribution are known.

Since it is important for an intracellular measurement of the local oxygen concentration and the local temperature distribution in an organism that the method is non-invasive, in particular optical methods for the oxygen and temperature determination are attractive and used at present. These techniques base on the phenomenon that the phosphorescence intensity of a phosphorescent compound and the delayed fluorescence intensity of a fluorescent compound change as a consequence of increased temperature or increased oxygen concentration. For example, a type of known temperature sensors contains two different luminophores, such as one phosphorescent compound and one fluorescent compound having energetically overlapping excited triplet states, wherein the phosphorescence of one of both compounds is strongly temperature dependent, whereas the delayed fluorescence of the other compound is also temperature dependent, but shows a substantially lower dependency. The ratio of the obtained luminescent intensities of both compounds then allows a determination of the temperature in a ratiometric response manner. Other techniques for non-invasive temperature sensing make use of nanogels, luminescent CdSe—CdS quantum dots as donors and cyanine dyes as acceptors or fluorescence polarization anisotropy of green fluorescent proteins. In all these techniques a ratiometric temperature response is achieved.

Known oxygen sensors, which are designed for detecting extremely low levels of oxygen, i.e. physiologically relevant oxygen concentrations ranging e.g. from 1 nM to 200 µM, base for instance on a transient state imaging technique or make use of single-nanoparticles with ratiometric oxygen response or of phosphorescent metalloporphyrins encapsulated in hydrophobic dendrimers.

However, temperature and oxygen responses in such sensors are interconnected, which leads to severe experimental complications. More specifically, a local temperature change is probably the single biggest source of error in optical sensors for oxygen. This is among others due to the fact that the temperature affects the fluorescence/phosphorescence quantum yield of phosphorescent compounds, the fluorescence/phosphorescence quenching constants, the solubility of oxygen in the sensor matrix, the diffusion of oxygen in the sensor matrix and the degree of singlet-triplet and triplet-singlet transitions in fluorescence/phosphorescence compounds. On other hand, the presence of even small traces of molecular oxygen, even in low ppm amounts, changes the response of a ratiometric phosphorescence temperature sensing system in a non-predictable manner. Furthermore, the oxygen sensing properties of an indicator dye are dependent on its microenvironment, such as for example the polymer matrix medium or sensor material, on its macro-environment and on the properties of the sample. On account of these reasons, the intracellular oxygen measurement performed with such techniques is falsified by the temperature influence, whereas the intracellular temperature measurement performed with such techniques is falsified by the oxygen influence of the techniques. Another disadvantage of the aforementioned optical techniques is that molecular oxygen (oxygen in ground state), i.e. triplet oxygen, which is present in the system, converts to a significant extent by a non-emissive process from an excited phosphorescent and/or fluorescent species into singlet oxygen, which is highly reactive and may harm the organism. A further disadvantage of specifically phosphorescence decay time measurement based methods is that they need an averaging of many excitation pulses, because the decay of phosphorescence is difficult to measure.

Accordingly, the object underlying the present invention is to provide a sensor, which is suitable to reliably, precisely and non-invasively measure the oxygen content and the temperature in a living object and in particular to perform such a measurement intracellularly with one measurement.

In accordance with the present invention, this object is satisfied by a capsule, preferably a nanocapsule, microcapsule or macrocapsule, which contains:
i) at least one first sensitizer compound having a triplet state with a first triplet energy band and being capable of energy transfer via an emissive process emitting light at a first frequency $v_1$ and being capable of energy transfer via a non-emissive process to triplet oxygen,
ii) as matrix material at least one compound being capable of reacting with singlet oxygen, wherein the at least one compound capable of reacting with singlet oxygen preferably comprises at least one terminal unsaturated carbon-carbon bond,
iii) at least one second sensitizer compound having a triplet state with a second triplet energy band and being capable of energy transfer via an emissive process and a non-emissive process and being capable of absorbing radiation at a second frequency $v_2$ and of emitting light at a fourth frequency $v_4$, iv) at least one emitter compound having a triplet state with a third triplet energy band, wherein the at least one second sensitizer compound is capable of transferring energy to the at least one emitter compound and wherein the at least one emitter compound, after obtaining energy transferred from the at least one second sensitizer compound, is capable of emitting light at a third frequency $v_3$, wherein the following equation is fulfilled: $v_3 > v_2$, wherein the at least one second sensitizer compound is capable of a triplet-triplet energy transfer to the at least one emitter compound and wherein the at least one emitter compound is capable of a triplet-triplet annihilation, wherein the upper energy limit of the first triplet energy band of the first sensitizer compound is lower than the lower energy limit of the second triplet energy band of the second sensitizer compound and lower than the lower energy limit of the third triplet energy band of the emitter compound, and wherein the third triplet band of the emitter compound at least partially overlaps with the second triplet energy band of the second sensitizer compound.

This solution bases on the surprising finding that by forming a capsule from at least one first sensitizer compound, at least one second sensitizer compound and at least one emitter compound being dispersed in a matrix, which is composed of at least one compound being capable of reacting with singlet oxygen, wherein the at least one compound capable of reacting with singlet oxygen preferably comprises at least one terminal unsaturated carbon-carbon bond, wherein the at least one first sensitizer compound is capable of energy transfer to triplet oxygen converting the triplet oxygen into singlet oxygen, wherein the upper energy limit of the first triplet energy band of the first sensitizer compound is lower than the lower energy limit of the second triplet energy band of the second sensitizer compound and lower than the lower energy limit of the third triplet energy band of the emitter compound, and wherein the third triplet band of the emitter compound at least partially overlaps with the second triplet energy band of the second sensitizer compound, a sensor is obtained, which allows to reliably, precisely and noninvasively measure the oxygen content as well as the temperature in a living object and in particular to perform such a measurement intracellularly with one measurement. While the first sensitizer compound in cooperation with the compound being capable of reacting with singlet oxygen allows a precise measurement of the oxygen content, the second sensitizer compound in cooperation with the emitter compound allows a precise measurement of the temperature, because the first sensitizer compound in cooperation with the compound being capable of reacting with singlet oxygen on the one hand and the second sensitizer compound in cooperation with the emitter compound on the other hand are decoupled from each other.

By irradiating the sample with radiation having an appropriate first wavelength (corresponding to the frequency $v_5$), the first sensitizer compound is excited by the absorbed energy first from the ground state into an excited singlet state. Thereafter, the excited singlet state non-radiatively transitions into an excited triplet state, which is called intersystem crossing. Thereby, the spin of the excited electron is reversed, so that the spin of the excited electron in the triplet state is no longer paired with the spin of the ground state electron. As a result thereof, the energy is trapped in the excited triplet state, because only classically forbidden transitions and thus kinetically unfavored transitions may lead to a return of the excited triplet state electron into the ground state with simultaneous emission of a photon. On account of this reason, the transition probability for the electron from the excited triplet state into the ground state is quite low, i.e. the triplet lifetime of the excited first sensitizer compound is comparable long. Due to the comparable long triplet state lifetime, the probability of a non-emissive energy transfer from the excited first sensitizer compound to triplet oxygen is quite high, as a consequence of which the excited first sensitizer compound is converted into the singlet ground state and the triplet oxygen is converted into singlet oxygen. This non-emissive energy transfer from the excited first sensitizer compound to triplet oxygen competes with the energy transfer from the excited first sensitizer compound via an emissive process leading to the emission of radiation at the first frequency wherein frequency $v_5$ is greater than frequency $v_1$. Of course, the frequency $v_1$ corresponds to a lower energy than the first wavelength of the applied radiation, because the triplet energy band of the first sensitizer compound is lower than the excited singlet state, into which the absorption of the radiation with the first wavelength excites the first sensitizer molecules. Since the probability of emission of the radiation at the first frequency $v_1$ due to phosphorescence is lower than the probability of non-emissive energy transfer from the excited first sensitizer compound to triplet oxygen (when molecular oxygen is present at the sample), the phosphorescence intensity is low or even zero as long as oxygen is present in the capsule, because all of the molecular oxygen is converted by the aforementioned non-emissive mechanism into singlet oxygen and all excited triplet states of the first sensitizer are lost. All of the generated singlet oxygen reacts immediately, i.e. within very short time after generation, with the terminal unsaturated carbon-carbon bonds of the matrix compound ii), whereby the oxygen is bonded by the matrix compound ii) and thus consumed immediately. On account of this, a contamination of the living object with reactive singlet oxygen is reliably avoided so that the method in accordance with the present invention is non-invasive and avoids oxidation damages in the living object. After conversion of all molecular oxygen into singlet oxygen and consumption of the generated singlet oxygen, the only possibility for the excited first sensitizer compound to return to its ground state is the emission of light with the first frequency $v_1$. Due to this, after consumption of the molecular oxygen, the phosphorescence intensity drastically increases, wherein the extent of time delay between the start of irradiation with radiation having the first wavelength and the start or drastic increase of phosphorescence with the first frequency $v_1$, respectively, and the number of the photons absorbed by the first sensitizer compound before the start or drastic increase of phosphorescence with the first frequency $v_1$ is proportional to the oxygen content in the capsule. Thus, the integral of the number of photons absorbed by the first sensitizer compound between the start of irradiation with radiation having the first wavelength and the start or drastic increase of phosphorescence with the first frequency $v_1$, respectively, is proportional to the oxygen content in the capsule. Accordingly, when the capsule is allowed to incubate in the living object before start of the measurement so long that the oxygen content outside the capsule is in equilibrium state with the oxygen content inside the capsule, the oxygen content at the desired location of the living object can be reliably determined with the capsule in accordance with the present invention.

Because the upper energy limit of the first triplet energy band of the first sensitizer compound is lower than the lower energy limit of the second triplet energy band of the second sensitizer compound and lower than the lower energy limit of the third triplet energy band of the emitter compound, the first sensitizer compound is with this respect decoupled from the second sensitizer compound and from the emitter compound, i.e. no non-emissive energy transfer between the first sensitizer compound and the second sensitizer compound and emitter compound, respectively, occurs. On account of this reason, the first sensitizer compound in cooperation with the compound being capable of reacting with singlet oxygen allows a precise measurement of the oxygen content by irradiating the capsule with radiation having the first wavelength without being disturbed by the second sensitizer compound and by the emitter compound. Moreover, apart from being due to the aforementioned reasons non-invasive, the capsule in accordance with the present invention allows to perform the oxygen measurement with a single measurement without needing repetitive measurements and averaging, such as in prior art methods.

After completion of the (first) oxygen measurement, the capsule is irradiated with radiation having a second wavelength for measuring the temperature. More specifically, the second wavelength is shorter than the first wavelength and the second wavelength is so as to excite the second sensitizer compound, wherein frequency $v_2$ is greater than frequency $v_5$. Thus, the second sensitizer compound is excited by the absorbed energy first from the ground state into an excited singlet state, which is converted by intersystem crossing into an excited triplet state. Due to the comparable long triplet state lifetime, the probability of a non-emissive energy transfer e.g. by Dexter energy transfer, which is called triplet-triplet energy transfer (TTT), from the excited second sensitizer compound to the emitter compound is quite high, because the third triplet band of the emitter compound at least partially overlaps with the second triplet energy band of the second sensitizer compound. However, it is required for such a triplet-triplet energy transfer that a second sensitizer molecule is in appropriate orientation for this energy transfer with the emitter compound. As a consequence of this energy transfer to the emitter, the excited second sensitizer compound molecule returns without emission into the ground state, whereas the emitter compound is excited into its triplet state. The aforementioned non-emissive triplet-triplet energy transfer from the excited second sensitizer compound to the emitter compound competes with the emissive energy transfer from the excited second sensitizer compound, i.e. with its phosphorescence (frequency $v_4$; $v_2 > v_4$). Two excited emitter molecules may then undergo a triplet-triplet annihilation (TTA), wherein the excited electron of one emitter molecule transfers its energy to the excited electron of the other emitter molecule. In other words, the excited electron of one emitter molecule returns during the triplet-triplet annihilation from the excited triplet state into the singlet ground state, whereas the excited electron of the other emitter molecule is transferred into a higher excited singlet state. Afterwards, the electron of the excited singlet state of the emitter compound returns into the ground state of the emitter molecule, whereby light with a third frequency $v_3$ is emitted. Due to the energy shift on account of the triplet-triplet annihilation, the third frequency $v_3$ of the emitted light is higher than the frequency $v_2$ initially absorbed by the second sensitizer compound. Since the mobility and in particular the rotational diffusion of both, the second sensitizer compound as well as of the emitter compound, increases with increasing temperature, the probability of the appropriate orientation of a second sensitizer molecule and an emitter molecule required for the energy transfer increases with increased temperature, why the probability of the triplet-triplet energy transfer and thus of triplet-triplet annihilation and emission of radiation with the third frequency $v_3$ from the emitter compound increases and thus the probability of residual phosphorescent ($v_4$) emission from the excited second sensitizer compound decreases. On account of this, with increased temperature the ratio of emission of radiation with the third frequency $v_3$ from the emitter compound to the emission of radiation with a lower frequency ($v_4$) from the second sensitizer compound increases. Accordingly, when the capsule is allowed to incubate in the living object before start of the measurement so long that the temperature inside the capsule is the same as that outside the capsule, the temperature at the desired location of the living object can be reliably determined with the capsule in accordance with the present invention.

Because the upper energy limit of the first triplet energy band of the first sensitizer compound is lower than the lower energy limit of the second triplet energy band of the second sensitizer compound and lower than the lower energy limit of the third triplet energy band of the emitter compound, so that the first triplet energy band of the first sensitizer compound does not overlap with the triplet energy bands of the second sensitizer and of the emitter compound, the second sensitizer and emitter compounds are with this respect decoupled from the first sensitizer compound. On account of this reason, the second sensitizer compound in cooperation with the emitter compound allows a precise measurement of the temperature by irradiating the capsule with radiation having the second wavelength without being disturbed by the first sensitizer compound.

All molecular energy levels involved in the processes, such as absorption, TTT, TTA, phosphorescence or delayed fluorescence emission, are real energetic levels and thus no virtual levels are involved. Accordingly, all described processes occur after intramolecular energy relaxation (thermalisation).

Ratiometric temperature response includes in general different dependence for the processes (residual sensitizer phosphorescence, emission of the frequency $v_4$) and TTA—upconversion (delayed fluorescence, emission of the frequency $v_3$) on the sample temperature.

All in all, the capsule in accordance with the present invention allows to non-invasively, precisely and reliably measure the oxygen content as well as the temperature intracellularly in a living object with one measurement by first irradiating the capsule with radiation having a first wavelength being compatible with the excitation energy of the first sensitizer compound for determining the oxygen content and by then irradiating the capsule with radiation having a second wavelength being compatible with the excitation energy of the second sensitizer compound for determining the temperature.

The term "triplet energy band" denotes that the triplet state of a photoactive compound has not only one defined energy level, but instead a plurality of triplet states with different energy levels. Thus, the term "triplet energy band" is intended to comprise all triplet states of one compound, wherein the lower energy limit of the triplet energy band is the energy level of the lowest triplet state of this compound, whereas the upper energy limit of the triplet energy band is the energy level of the highest triplet state of this compound.

As set out above, it is an important feature of the present invention that the third triplet band of the emitter compound at least partially overlaps with the second triplet energy band of the second sensitizer compound. Preferably, the lower energy limit of the third triplet band of the emitter compound is equal to or lower than the lower energy limit of the second triplet energy of the second sensitizer compound.

In accordance with the present invention, the capsule may include as first sensitizer compound any photoactive compound having a triplet state with a first triplet energy band and being capable of emitting light at a first frequency $v_1$ and being capable of energy transfer to triplet oxygen. However, since the upper energy limit of the first triplet energy band of the first sensitizer compound has to be lower than the lower energy limit of the second triplet energy band of the second sensitizer compound and lower than the lower energy limit of the third triplet energy band of the emitter compound, it is preferred that the first sensitizer compound has a triplet energy band, wherein the upper energy limit of the triplet energy band is comparable low.

Taking this into account, suitable examples for the first sensitizer compound are compounds selected from the group consisting of monoanthra[2,3]porphyrins, dianthra[2,3]porphyrins, trianthra[2,3]porphyrins, tetraanthra[2,3]porphyrins and arbitrary combinations of two or more of the aforementioned compounds.

In an alternative preferred embodiment, the capsule in accordance with the present invention contains as first sensitizer compound at least one compound selected from the group consisting of mixed benzo- and naphtho-[2,3]porphyrins, mixed benzo- and anthra-[2,3]porphyrins, mixed naphtho- and anthra[2,3]porphyrins and mixed benzo-, naphtho and anthra-[2,3]porphyrins.

Particularly good results are obtained, when at least one and preferably all of the at least one first sensitizer compound(s) is/are a compound according to any of the following general formulae (1) to (13):

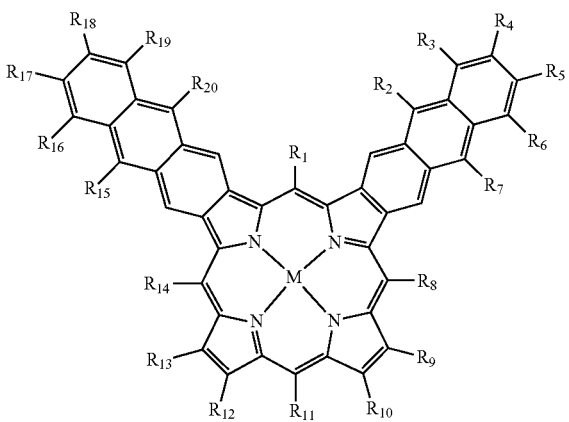

2

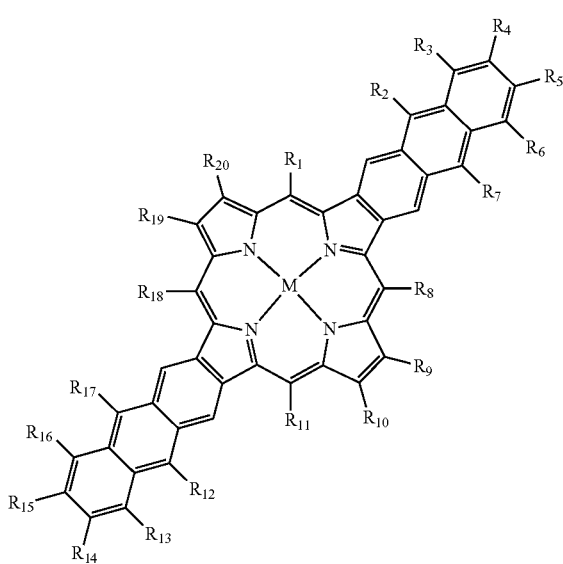

3

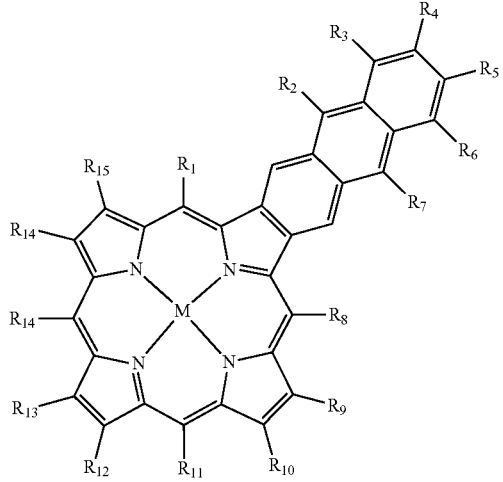

1

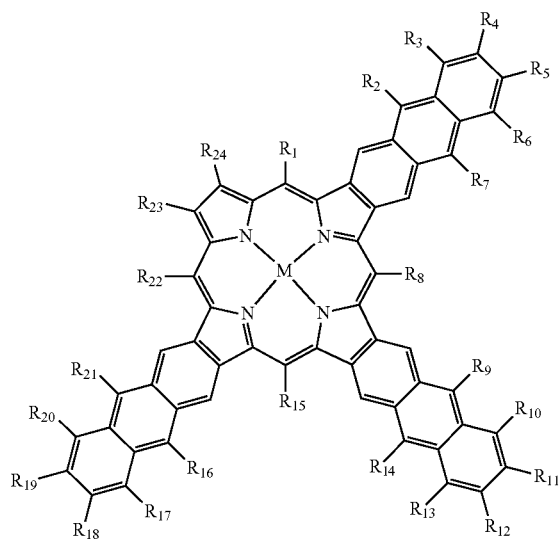

4

5
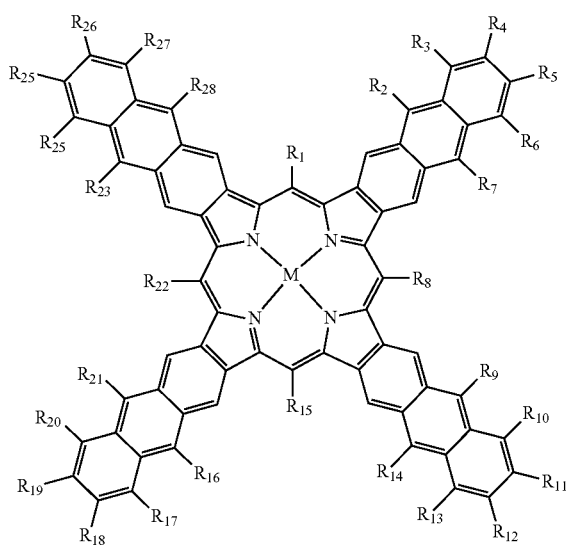
6
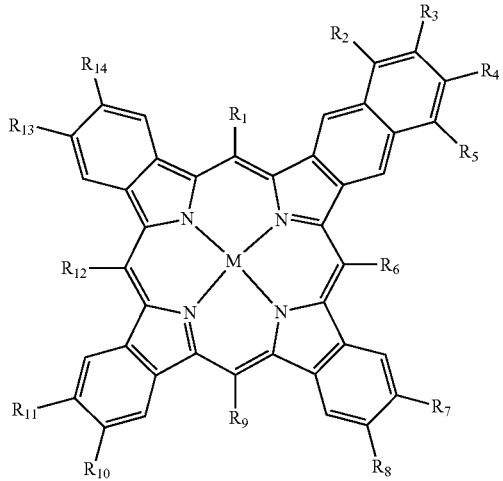
7
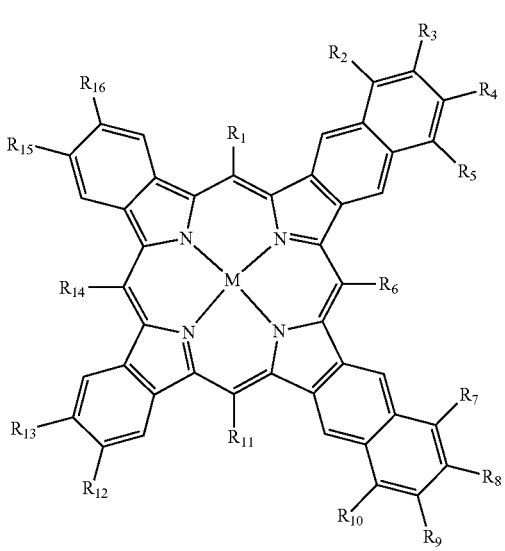
8
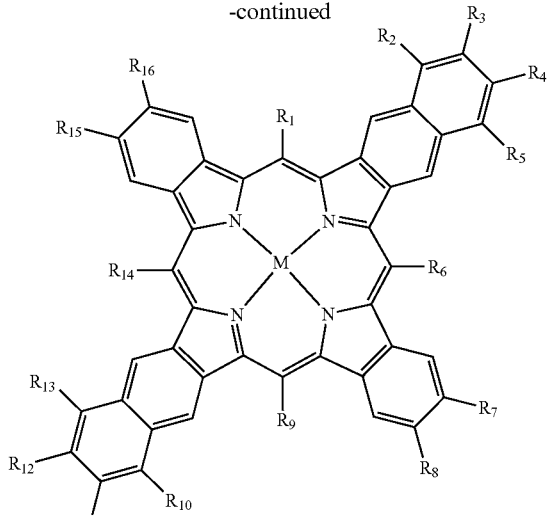
9
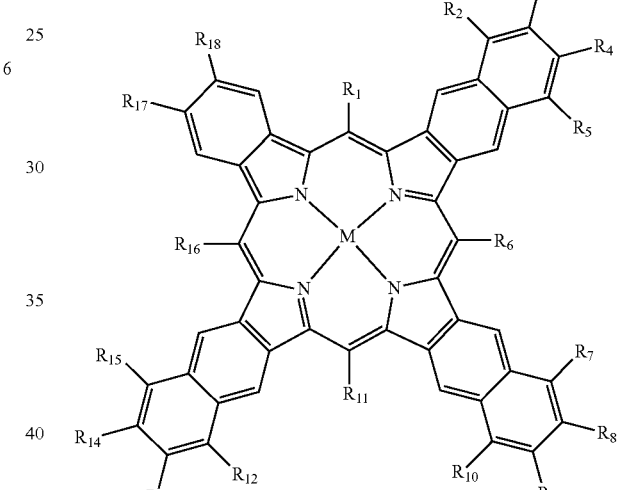
10
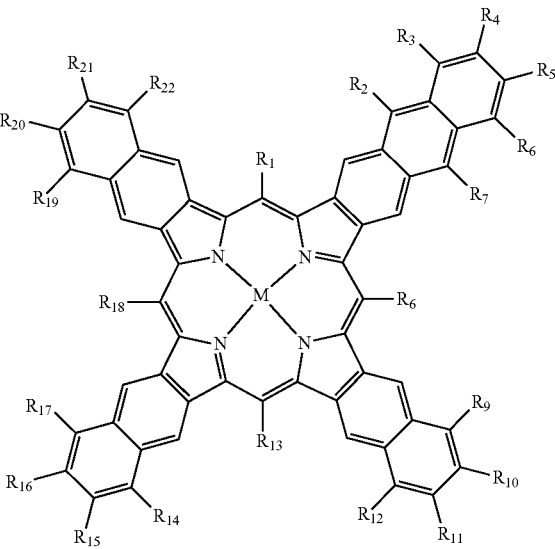

-continued

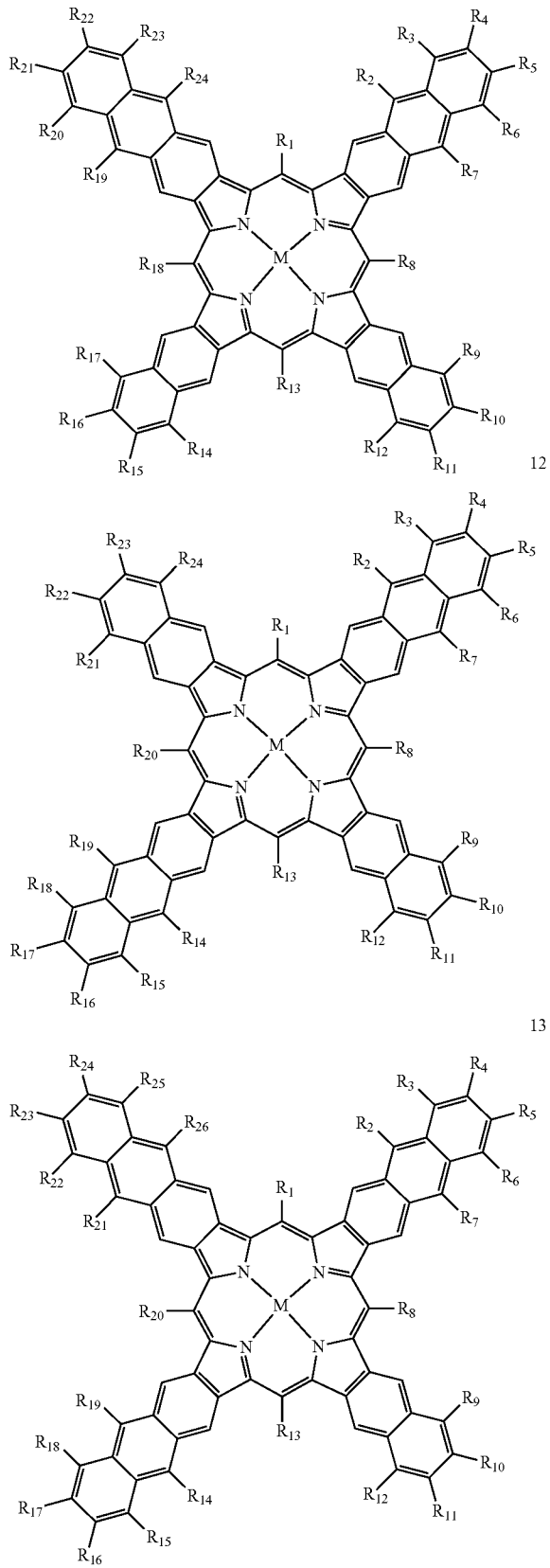

11

12

13 wherein
any of residues $R_1$ to $R_{28}$ is independently selected from the group consisting of hydrogen, alkyl, alkenyl, alkynyl, aryl, carboxy, alkoxy, alkylthio, aryloxy, arylthio, alkoxycarbonyl, aryloxycarbonyl, alkylcarbonyl, arylcarbonyl, halogen, amino, alkylamino, arylamino, amide with alkyl and/or aryl groups, sulfonyl, alkylsulfonyl and arylsulfonyl and M is selected from the group consisting of zinc, copper, nickel, magnesium, iron, cadmium, tin, lead, palladium, platinum, ruthenium, rhenium, iridium, osmium, gold, bismuth and uranium.

It has to be noted that all of the groups mentioned above for the residues $R_1$ to $R_{28}$ may carry additional linear or branched alkyl groups for improving the solubility of the compounds in organic solvents, negatively charged groups, such as sulfate or carboxyl groups, positively charged groups, such as ammonium, or neutral water-solubilizing groups, such as polyethylene glycol or polyvinyl alcohol chains, for improving the water solubility. Moreover, the metal may carry additional ligands, like chloride, bromide, oxygen, amine groups, phosphine groups, heterocyclic aromatic groups, β-diketone groups or the like.

In further development of the idea in accordance with the present invention, it is proposed that at least one and preferably all of the at least one first sensitizer compound(s) is/are a compound according to any of the following general formulae (1) to (13), wherein any of the residues $R_1$ to $R_{28}$ is independently selected from the group consisting of hydrogen, fluorine, $C_{1-8}$-alkyl, $C_{1-8}$-alkenyl, $C_{1-8}$-alkynyl and 0612-aryl, and M is palladium or platinum.

Particularly suitable examples for the first sensitizer compound are 5,10,15,20-tetra([1,1'-biphenyl]-4-yl)tetraanthra[2,3]porphyrin palladium(II), 5,10,15,20-tetraphenyl-$2^5,2^6,2^7,2^8,7^5,7^6,7^7,7^8,12^5,12^6,12^7,12^8,17^5,17^6,17^7,17^8$-hexadecafluorotetraanthra[2,3]porphyrin platinum(II), 5,10,15,20-tetraphenyltribenzomononaphto[2,3]porphyrin palladium(II) and 5,10,15,20-tetraphenyltrinaphtomonoanthra[2,3]porphyrin palladium(II).

In order to allow an efficient and fast energy transfer from the first sensitizer compound to molecular oxygen, the first sensitizer compound is preferably homogenously dispersed in the matrix composed of the at least one compound being capable of reacting with singlet oxygen and optionally further matrix material(s). In order to fulfill this function, the concentration of the first sensitizer compound in the capsule should not be too low, but also not too high in order to have enough volume for the other ingredients. Good results are in particular obtained, when the concentration of the all of the at least one first sensitizer compound in the capsule is $10^{-3}$ to $10^{-6}$ mol/l, more preferably $5 \cdot 10^{-4}$ to $5 \cdot 10^{-5}$ mol/l and even more preferably $2,5 \cdot 10^{-4}$ to $2,5 \cdot 10^{-5}$ mol/l, such as about $1 \cdot 10^{-4}$ mol/l.

In principle, the capsule in accordance with the present invention may include as matrix compound being capable of reacting with singlet oxygen any compound, which comprises at least one terminal unsaturated carbon-carbon bond and which is able to react with singlet oxygen so that the singlet oxygen is consumed or inactivated, respectively. Good results are obtained, when at least one of and preferably all of the at least one compound being capable of reacting with singlet oxygen—which is subsequently also referred to as singlet oxygen inhibitor—is selected from the group consisting of compounds having anyone of the following general formulae (I) to (X):

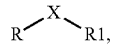
(I)

wherein
X is O or S,
R is alkenyl or alkynyl and
R1 is H, alkyl, ether-alkyl, ether-alkenyl, alkenyl, alkynyl, aralkyl, aryl or heteroaryl,

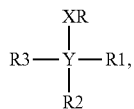
(II)

wherein
X is O or S,
R is alkenyl or alkynyl,
Y is alkyl, alkenyl, alkynyl, aralkyl, aralkenyl, aralkynyl, aryl or heteroaryl and
R1, R2, R3 are independently from each other H, XR, alkyl, ether-alkyl, ether-alkenyl, alkenyl, alkynyl, aralkenyl, aralkynyl, aralkyl, aryl or heteroaryl, wherein X and R are as defined above,

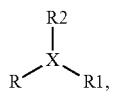
(III)

wherein
X is N or P,
R is alkenyl or alkynyl and
R1 and R2 are independently from each other H, alkyl, alkenyl, alkynyl, aralkyl, aryl or heteroaryl,

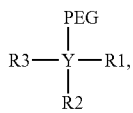
(IV)

wherein
PEG is an oligoethylene glycol or polyethylene glycol group having 2 to 99 ethylene glycol units,
R1 is alkenyl or alkynyl,
Y is Si and
R2 and R3 are independently from each other H, COOR, alkyl, alkenyl, alkynyl, aralkyl, aryl, heteroaryl or XR4, wherein X is N, P or As and R, R4 are independently from each other alkenyl or alkynyl,

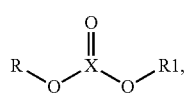
(V)

wherein
X is P, S, B or Si,
R is alkenyl or alkynyl and
R1 is H, alkyl, alkenyl, alkynyl, aralkyl, aryl or heteroaryl,

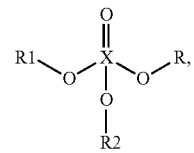
(VI)

wherein
X is P, S, B or Si,
R is alkenyl or alkynyl and
R1 and R2 are independently from each other H, alkyl, alkenyl, alkynyl, aralkyl, aryl or heteroaryl,

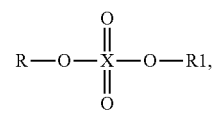
(VII)

wherein
X is P, S, B or Si,
R is alkenyl or alkynyl and
R1 is H, alkyl, alkenyl, alkynyl, aralkyl, aryl or heteroaryl,

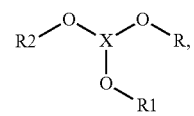
(VIII)

wherein
X is P, S, B or Si,
R is alkenyl or alkynyl and
R1 and R2 are independently from each other H, alkyl, alkenyl, alkynyl, aralkyl, aryl or heteroaryl,

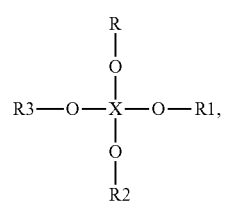
(IX)

wherein
X is P, S, B or Si,
R is alkenyl or alkynyl and
R1, R2 and R3 are independently from each other H, alkyl, alkenyl, alkynyl, aralkyl, aryl or heteroaryl,

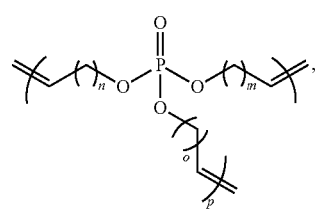
(Xa)

wherein
n, m and o are independently from each other an integer between 1 and 20 and
p is an integer of 2 or more,

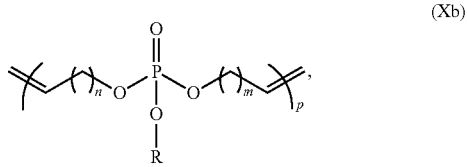

(Xb)

wherein
R is H, alkyl, alkenyl, alkynyl, aralkyl, aryl or heteroaryl,
n and m are independently from each other an integer between 1 and 20 and
p is an integer of 2 or more
or

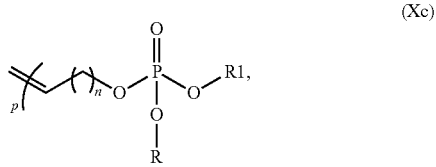

(Xc)

wherein
R and R1 are independently from each other H, alkyl, alkenyl, alkynyl, aralkyl, aryl
or heteroaryl,
n is an integer between 1 and 20 and
p is an integer of 2 or more.

Particularly good results are obtained, when the at least one compound capable of reacting with singlet oxygen has one of the aforementioned general formulae (I) to (III) and (V) to (IX), in which R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl and preferably in which R is selected from the group consisting of allyl, 3-buten-1-yl, 4-penten-1-yl, 5-hexen-1-yl, 10-undecen-1-yl. Likewise, it is preferred when the at least one compound capable of reacting with singlet oxygen has the general formula (IV), in which $R_1$ is selected from the above identified group. These residues have an appropriate chain length and degree of hydrophobicity leading to a very good reactivity with singlet oxygen, to a good solubility for the photoactive compounds i), iii), and iv). Due to this, the singlet oxygen inhibitor is simultaneously a good solvent and matrix for the photoactive compounds.

More preferably, when the at least one compound capable of reacting with singlet oxygen has the general formula (I) or the general formula (II), X is oxygen or sulfur, R is alkenyl (preferably one of the aforementioned preferred one) and $R_1$ in formula (I) or Y, $R_1$, $R_2$, $R_3$ in formula (II), respectively, are as defined above for formulae (I) and (II). Even better results are obtained with this regard, if the at least one compound capable of reacting with singlet oxygen in the composition has the general formula (I), in which X is oxygen, R is alkenyl and R1 is H, $C_{1-6}$-alkyl or $(CH_2)_n$—O—$(CH_2)_m$, wherein m and n are independently from each other integers of 1 or more. Most preferably, in the embodiment, in which the at least one compound capable of reacting with singlet oxygen has the general formula (I), X is oxygen, R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl and R1 is H. One particular preferred example therefor is 5-hexene-1-ol.

It is even more preferred that the composition in accordance with the present invention contains as at least one of the at least one compound capable of reacting with singlet oxygen a compound having the general formula (II), in which X is oxygen, R is alkenyl, Y is $C_{1-6}$-alkyl, $C_{6-12}$-aryl or $C_{6-12}$-heteroaryl and $R_1$, $R_2$, $R_3$ are independently from each other H, XR, alkyl, ether-alkyl, ether-alkenyl, alkenyl or alkynyl, wherein X is oxygen and R is alkenyl. Particular preferably, X is oxygen, R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl, Y is $C_{1-6}$-alkyl or phenyl and R1, R2, R3 are independently from each other H and XR, wherein X is oxygen and R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl.

In an alternative embodiment of the present invention, the at least one compound capable of reacting with singlet oxygen has the general formula (III), wherein X is nitrogen or phosphorus, R is alkenyl and $R_1$ and $R_2$ are independently from each other preferably H or alkenyl. More preferably, X is phosphorus, R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl and $R_1$ and R2 are independently from each other H or selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl.

In a further alternative embodiment of the present invention, the at least one compound capable of reacting with singlet oxygen has the general formula (IV), in which PEG is an oligoethylene glycol or polyethylene glycol group having 2 to 99 ethylene glycol units, $R_1$ is alkenyl, Y is Si and $R_2$, $R_3$ are independently from each other H, COOR, alkyl, alkenyl, alkynyl, aryl, heteroaryl or $XR_4$, wherein X is N or P and R, $R_4$ are independently from each other alkenyl. Notably good results are in particular obtained, when $R_1$ is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl, Y is Si and $R_2$, $R_3$ are independently from each other H, COOR, XR4 or alkenyl selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl, wherein X is N or P and R, $R_4$ are independently from each other selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl.

In an alternative and particularly preferred embodiment of the present invention, the at least one compound capable of reacting with singlet oxygen has any of the general formulae (V) to (IX), wherein X is P, S, B or Si, R is alkenyl and R1, R2, R3 are independently from each other H, $C_{1-10}$-alkyl, $C_{1-10}$-alkenyl, $C_{6-18}$-alkylaryl or $C_{6-12}$-aryl. More preferably, X is P, S, B or Si, R is alkenyl selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl and R1, R2 and R3 are independently from each other H, $C_{3-8}$-alkyl, phenyl or alkenyl selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl. Particular good results are obtained with this regard, when the compound capable of reacting with singlet oxygen has the general formula (VII), wherein X is S, R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl and R1 is $C_{3-8}$-alkyl, phenyl or alkenyl selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl.

Even better results are obtained with this regard, when the compound capable of reacting with singlet oxygen has the general formula (VI), wherein X is P, R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl, and $R_1$ and R2 are independently from each other $C_{3-8}$-alkyl, phenyl or alkenyl selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl.

According to still another preferred embodiment of the present invention, the composition in accordance with the present invention contains as compound capable of reacting with singlet oxygen at least one compound, which has the general formula (VIII), wherein X is B, R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl and $R_1$ and R2 are independently from each other $C_{3-8}$-alkyl, phenyl or alkenyl selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl.

According to still another preferred embodiment of the present invention, the composition in accordance with the present invention contains as compound capable of reacting with singlet oxygen at least one compound, which has the general formula (IX), wherein X is Si, R is selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl and R1, R2 and R3 are independently from each other $C_{3-8}$-alkyl, phenyl or alkenyl selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl. Even more preferably, R1, R2 and R3 are independently from each other phenyl or alkenyl selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl and still more preferably, R1, R2 and R3 are independently from each other selected from the group consisting of allyl, 3-buten-1-yl, 4-penten-1-yl, 5-hexen-1-yl, 6-hepten-1-yl, 7-octen-1-yl, 8-nonen-1-yl, 9-decen-1-yl and 10-undecen-1-yl. Likewise to the aforementioned phosphate and borate compounds, such silicate compounds also have a good reactivity with singlet oxygen.

Suitable individual examples for compounds according to the general formulae (V) to (IX) are diallyl phenyl phosphate, di(10-undecenyloxy)phenyl phosphate, di(3-buten-1-yl)phenyl phosphate, triallyl phenyl phosphate, tri(10-undecen-1-yl) phosphate, tri(5-hexen-1-yl) phosphate, tetra(5-hexen-1-yl)orthosilicate, tri(5-hexen-1-yl) borate, di(hex-5-en-1-yl)sulfate and arbitrary combinations of two or more of these compounds.

According to a further, even more preferred embodiment of the present patent application, the composition contains as compound capable of reacting with singlet oxygen at least one compound according to the general formula (Xa), wherein n, m and o are independently from each other an integer between 1 and 10 and p is an integer of 2 to 120, or according to the general formula (Xb), wherein R is an aryl and preferably a phenyl, n and m are independently from each other an integer between 1 and 10 and p is an integer of 2 to 120, or according to the general formula (Xc), wherein R and R1 are independently from each other an aryl and preferably a phenyl, n is an integer between 1 and 10 and p is an integer of 2 to 120. Such hyperbranched phosphoester compounds do not only have a sufficiently high degree of hydrophobicity and viscosity allowing the compound to be a good solvent for the at least one compound, but also provide a very high number of double bonds per molecule, which are able to react with singlet oxygen, so that these compounds are also very effective singlet oxygen inhibitors and have a high singlet oxygen inhibition capacity. Moreover, these hyperbranched phosphoester compounds act as excellent matrix material for the photoactive compounds i), iii) and iv). In addition to terminal carbon-carbon double bonds, these compounds also comprise internal carbon-carbon double bonds. Due to all these properties, the compounds according to the general formula (X) and in particular those according to the general formula (Xa), in which n, m and o are independently from each other integers between 1 and 10 and p is an integer of 2 to 120, are most preferred as compounds ii) of the capsule in accordance with the present patent application.

Preferably, m, n and o are an integer between 2 and 11 and even more preferably m, n and o are an integer between 4 and 11 in the aforementioned formula (Xa). Likewise to this, m and n are preferably an integer between 2 and 11 and even more preferably m and n are an integer between 4 and 11 in the aforementioned formula (Xb). Likewise to this, n is preferably an integer between 2 and 11 and even more preferably n is an integer between 4 and 11 in the aforementioned formula (Xc). Notably good results are obtained, when p is an integer between 3 and 40 in the aforementioned formulae (Xa), (Xb) and (Xc). Furthermore, the hyperbranched phosphoester compounds according to any of the formulae (Xa), (Xb) and (Xc) have preferably a total number of terminal unsaturated carbon-carbon bonds per molecule of 4 or more, more preferably between 4 and 122 and even more preferably between 5 and 42.

Notably good examples of these compounds are:

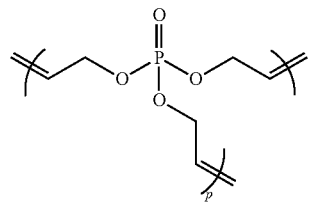 (XI)

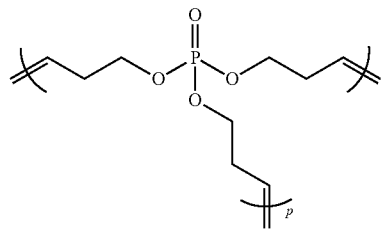 (XII)

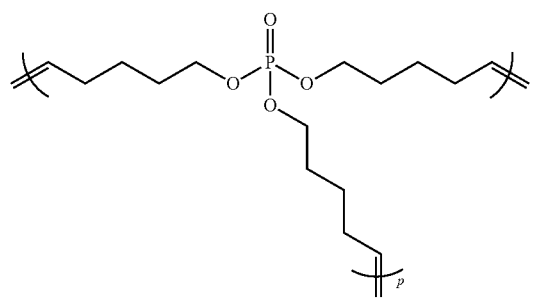 (XIII)

and

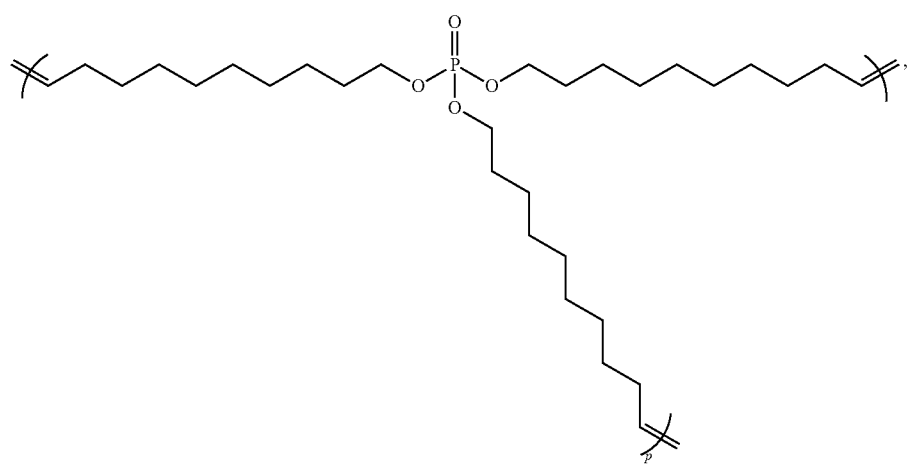 (XIV)

wherein in each of these formulae p is an integer of 2 to 120 and preferably p is an integer of 3 to 40.

In order to be present in a sufficient excess so as to allow to inactivate singlet oxygen over a long operation time immediately after generation, it is further preferred that the number of terminal unsaturated carbon-carbon bonds of the at least one compound being capable of reacting with singlet oxygen is contained in the composition in such an amount that the number of terminal unsaturated carbon-carbon bonds of the at least one compound capable of reacting with singlet oxygen is at least 100 times, preferably at least 1,000 times, more preferably at least 10,000 times, even more preferably at least $10^5$ times, even more preferably at least $10^6$, even more preferably at least $10^7$ times and most preferably at least $10^8$ times higher in the composition than the number of molecules of all of the at least one first sensitizer compound.

In accordance with the present invention, the second sensitizer compound has a triplet energy band with a lower energy limit, which is higher than the upper energy limit of the first triplet energy band of the first sensitizer compound. Good results are in particular obtained, when at least one of and more preferably all of the at least one second sensitizer compound is/are a compound according to any of the following general formulae (14) to (19):

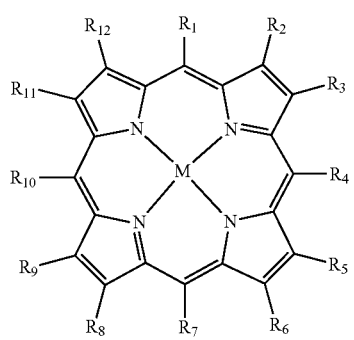

14

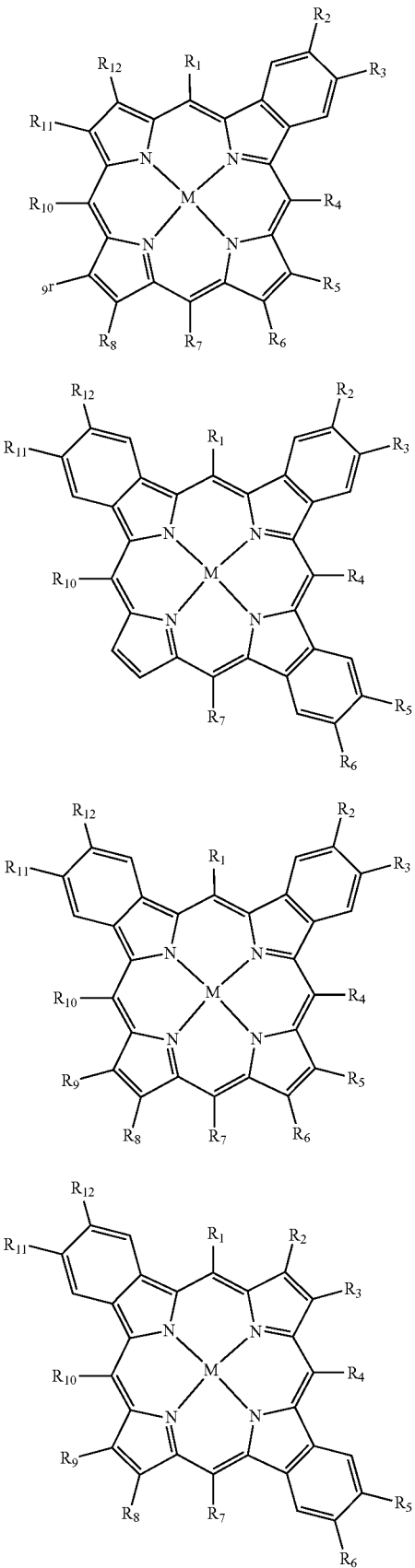

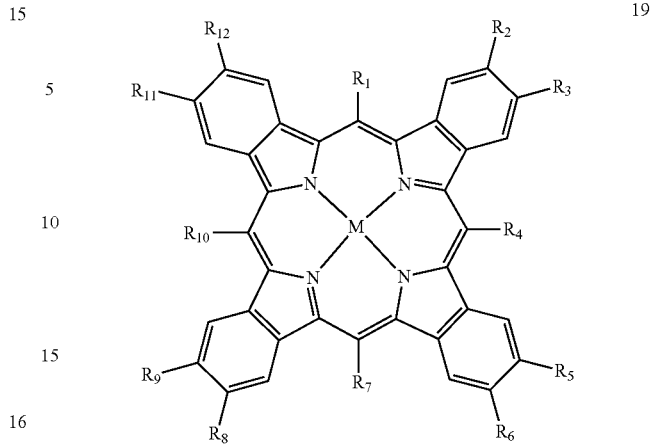

wherein
in any of these formulae any of residues $R_1$ to R12 is independently selected from the group consisting of hydrogen, alkyl, alkenyl, alkynyl, aryl, carboxy, alkoxy, alkylthio, aryloxy, arylthio, alkoxycarbonyl, aryloxycarbonyl, alkylcarbonyl, arylcarbonyl, halogen, amino, alkylamino, arylamino, amide with alkyl and/or aryl groups, sulfonyl, alkylsulfonyl and arylsulfonyl, and M is selected from the group consisting of zinc, copper, nickel, magnesium, iron, cadmium, tin, lead, palladium, platinum, ruthenium, rhenium, iridium, osmium, gold, bismuth and uranium.

In this embodiment, all of the groups mentioned above for the residues $R_1$ to $R_{12}$ may carry additional linear or branched alkyl groups for improving the solubility of the compounds in organic solvents, negatively charged groups, such as sulfate or carboxyl groups, positively charged groups, such as ammonium, or neutral water-solubilizing groups, such as polyethylene glycol or polyvinyl alcohol chains, for improving the water solubility. Moreover, the metal may carry additional ligands, like chloride, bromide, oxygen, amine groups, phosphine groups, heterocyclic aromatic groups, β-diketone groups or the like.

Particularly suitable examples for the second sensitizer compound are 5,10,15,20-tetraphenylporphyrin palladium (II), 5,10,15,20-tetra(anthracen-9-yl) porphyrin platinum (II), 5,10,15,20-tetraphenylethynylporphyrin palladium(III) chloride, 2,3,7,7,12,13,17,18-octaethylporphyrin palladium (II), 5,10,15,20-tetraphenylhexadecahydrotetrabenzoporphyrin platinum (II), 5,10,15,20-tetraphenyltetrabenzoporphyrin palladium(II), 5,10,15,20-tetra(3,5-dicarboxyphenyl) tetrabenzoporphyrin platinum(II) and $2^2,2^3,5,7^2,7^3,10,12^2,12^3,15,17^2,17^3,20$-dodecaphenyltetrabenzoporphyrin copper(II).

According to a further preferred embodiment of the present invention, the concentration of the at least one second sensitizer compound in the capsule is $10^{-3}$ to $10^{-6}$ mol/l, more preferably $5·10^{-4}$ to $5·10^{-5}$ mol/l and even more preferably $2,5·10^{-4}$ to $2,5·10^{-5}$ mol/l, such as about $1·10^{-4}$ mol/l. In order to allow an efficient and fast energy transfer from the second sensitizer compound to the emitter compound, the second sensitizer compound is preferably homogenously dispersed in the matrix.

In principle, the capsule may include all emitter compounds having a triplet energy band with a lower energy limit, which is higher than the upper energy limit of the first triplet energy band of the first sensitizer compound, wherein the triplet band of the emitter compound at least partially overlaps with the second triplet energy band of the second sensitizer compound. Good results are particularly obtained, when at least one of and more preferably all of the at least one emitter compound is/are a compound according to any of the following general formulae (20) to (24):

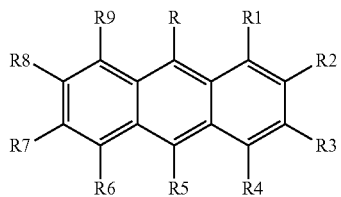

20

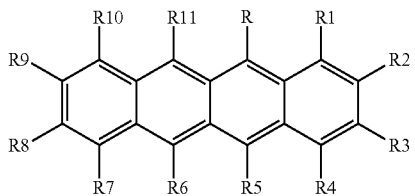

21

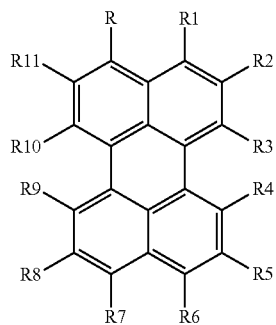

22

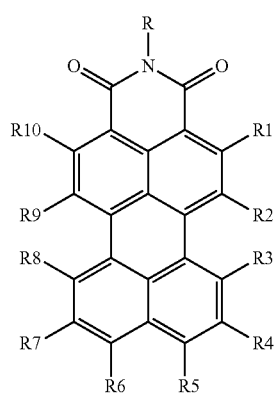

23

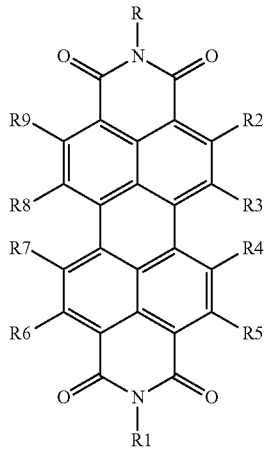

24 wherein
in any of these formulae any of residues R, $R_1$ to $R_{11}$ is independently selected from the group consisting of hydrogen, alkyl, alkenyl, alkynyl, aryl, carboxy, alkoxy, alkylthio, aryloxy, arylthio, alkoxycarbonyl, aryloxycarbonyl, alkylcarbonyl, arylcarbonyl, halogen, amino, alkylamino, arylamino, amide with alkyl and/or aryl groups, sulfonyl, alkylsulfonyl and arylsulfonyl.

Also in this embodiment, all of the groups mentioned above for the residues R, $R_1$ to $R_{11}$ may carry additional linear or branched alkyl groups for improving the solubility of the compounds in organic solvents, negatively charged groups, such as sulfate or carboxyl groups, positively charged groups, such as ammonium, or neutral water-solubilizing groups, such as polyethylene glycol or polyvinyl alcohol chains, for improving the water solubility. Moreover, the metal may carry additional ligands, like chloride, bromide, oxygen, amine groups, phosphine groups, heterocyclic aromatic groups, 6-diketone groups or the like.

Particularly suitable examples for the first sensitizer compound are 5-phenylanthracene, 5,10-diphenylanthracene, 5,10-bis(phenylethynyl)anthracene, 5-phenyltetracene, 5,11-diphenyltetracene, 5,11-bis(phenylethynyl)tetracene, rubrene, 3-(4-tert-butylphenyl)perylene, 3-(3,3'-dimethylbutynyl)perylene, 3-((4-tert-butylphenyl)ethynyl)perylene, 3,10-bis(4-tert-butylphenyl)perylene, 3,10-bis((4-tert-butylphenyl)ethynyl)perylene, 3,10-di(3,3'-dimethylbutynyl)perylene, potassium perylene-3,4,9,10-tetracarboxylate, tetra-3,4,9,10(ethoxycarbonyl)perylene, N-(2,6-diisopropylphenyl)-perylene-3,4-dicarboximide, 9-(4-tertbutylphenyl)-N-(2,6-diisopropyl-phenyl)perylene-3,4-dicarboximide, 9-(3,3'-Dimethylbutynyl)-N-(2,6-diisopropyl-phenyl)perylene-3,4-dicarboximide, 1,6,9-tris(3,3'-Dimethylbutynyl)-N-(2,6-diisopropylphenyl)perylene-3,4-dicarboximide, N,N'-Bis(2,6-diisopropylphenyl)-perylene-3,4:9,10-bis(dicarboximide), N,N'-bis(2,6-diisopropylphenyl)-1,7-bis(4-tert-butylphenoxy)perylene-3,4:9,10-bis(dicarboximide), N,N'-bis(2,6-diisopropylphenyl)-1,7-bis(3,3'-dimethylbutynyl)perylene-3,4:9,10-bis(dicarboximide) and N,N'-bis(2,6-diisopropylphenyl)-1,6,7,12-tetraphenoxyperylene-3,4:9,10-bis(dicarboximide).

According to a further preferred embodiment of the present invention, the concentration of the at least one emitter compound in the capsule is $2 \cdot 10^{-3}$ to $1 \cdot 10^{-6}$ mol/l, more preferably $1 \cdot 10^{-3}$ to $1 \cdot 10^{-5}$ mol/l and even more preferably $2\cdot10^{-4}$ to $8\cdot10^{-4}$ mol/l, such as about $5\cdot10^{-4}$ mol/l. In order to allow an efficient and fast energy transfer from the second sensitizer compound to the emitter compound, the emitter compound is preferably homogenously dispersed in the matrix.

In accordance with a particularly preferred embodiment of the present invention, the capsule contains a further matrix material v). The purpose of the further matrix material is to increase the temperature dependence of the matrix in order to increase the sensitivity of the capsule for temperature measurements. Preferably, the further matrix material has in the interesting temperature range (of the sensor), which is for example between +5 and +40° C., a comparable high viscosity dependency from the temperature and in particular has in the interesting temperature range a comparable high decrease of its viscosity per degree Celsius temperature increase. On account of the comparable strong decrease of the viscosity of the further matrix material the mobility and in particular the rotational diffusion of both, the second sensitizer compound as well as of the emitter compound, increases in the matrix with increasing temperature so that the probability of an appropriate orientation of the second sensitizer molecules and the emitter molecules for an energy transfer from the second sensitizer to the emitter significantly increases with increasing temperature. Thus, when irradiating the capsule with radiation with the second wavelength the ratio of emission of radiation with the third frequency $v_3$ from the emitter compound to the emission of radiation with a lower frequency $v_4$ from the second sensitizer compound reliably allows to determine the temperature.

In order to be sensitive in the temperature range relevant for living objects, the further matrix material has preferably a melting point between 20 and 120° C.

Moreover it is preferred that the further matrix material is selected from the group consisting of waxes, esters derived from a fatty acid and a fatty alcohol having one to four hydroxyl groups, triglycerides, glycol esters, polymers and arbitrary mixtures of two or more of the aforementioned compounds.

Suitable waxes are those selected from the group consisting of paraffin waxes, beeswaxes, carnauba waxes and ozokerite. If a solid ester is used, the ester is preferably derived from a fatty acid, for example cetyl palmitate, and a fatty alcohol, which may have one, two, three or four hydroxyl groups, such as ethylene glycol and glycerol. As triglyceride for example a triglyceride comprising saturated fatty acids, such as lauric acid, myristic acid and/or stearic acid, may be used.

Suitable examples for glycol esters are solid esters of a diol, such as ethylene glycol, propylene glycol and the like, and saturated fatty acids, such as lauric acid, myristic acid and/or stearic acid. As polymers for example polystyrene may be used. If a polymer is used, its glass transition temperature is preferably between 20 and 120° C.

In addition, it is preferred that the weight ratio of the further matrix material to the sum of the at least one compound being capable of reacting with singlet oxygen and the further matrix material in the capsule is 1 to 99%, more preferably 10 to 90%, even more preferably 25 to 75% and most preferably 40 to 60%, such as in particular about 50%.

In accordance with a further particularly preferred embodiment of the present invention, the capsule comprises a core including the components i) to iv) and the optional further matrix material v), wherein the core is encapsulated by a shell.

Good results are in particular obtained, when the shell is oxygen permeable, in order to allow that an oxygen distribution equilibrium between the environment outside the capsule and the interior of the capsule is adjusted.

Depending on the purpose, the capsule may have a diameter of 1 to 5,000 nm and preferably of 150 to 500 nm Principally, the present invention is not limited concerning the material of the shell of the capsule. For example, the shell may be composed of a polymer, such as a petrochemical polymer or a natural polymer, of a metal oxide or of a hybrid material formed by an arbitrary mixture of polymer and metal oxide.

A further aspect of the present invention is the use of the above described capsule as an oxygen sensor or as a temperature sensor and preferably simultaneously as an oxygen and temperature sensor.

Subsequently, the present invention is exemplified by means of a non-limiting example.

EXAMPLE

A nanocapsule with the following components have been prepared:
first sensitizer: tetraaryltetranaphto[2,3]porphyrin Pd (PdTNP) in a concentration of $1\cdot10^{-4}$ mol/l,
second sensitizer: tetraaryltetrabenzo[2,3]porphyrin Pd (PdTBP) in a concentration of $1\cdot10^{-4}$ mol/l,
emitter: perylene in a concentration of $2\cdot10^{-3}$ mol/l,
first matrix material, i.e. compound being capable of reacting with singlet oxygen: di(5-hexen-1-yl) phenyl phosphate in an amount of 50% by weight and
second matrix material: paraffin wax having a melting point of 44° C. in an amount of 50% by weight.

FIG. 1 shows the simplified energetic schema for the oxygen and temperature measurement with the aforementioned nanocapsule including PdTNP/PdTBP/perylene/paraffin wax/di(5-hexen-1-yl) phenyl phosphate.

Figure 2:
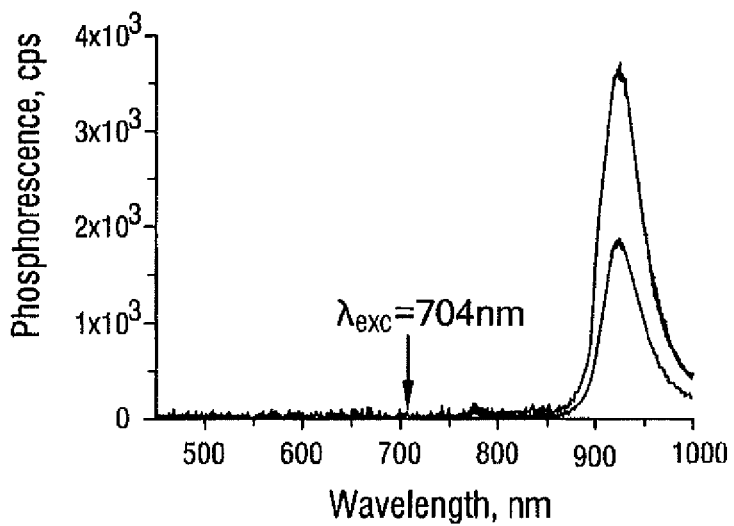

FIG. 2 shows the scavenging of molecular oxygen in the aforementioned nano-encapsulated oxygen and temperature sensor including PdTNP/PdTBP/perylene/paraffin wax/di(5-hexen-1-yl) phenyl phosphate in water by showing the intensities of phosphorescence at glove box conditions with the aforementioned nanocapsule at 50 ppm oxygen concentration in the sample chamber (curve A) and after 5 seconds of irradiating the sample with radiation having the frequency $v_5$ (curve B).

Figure 3:
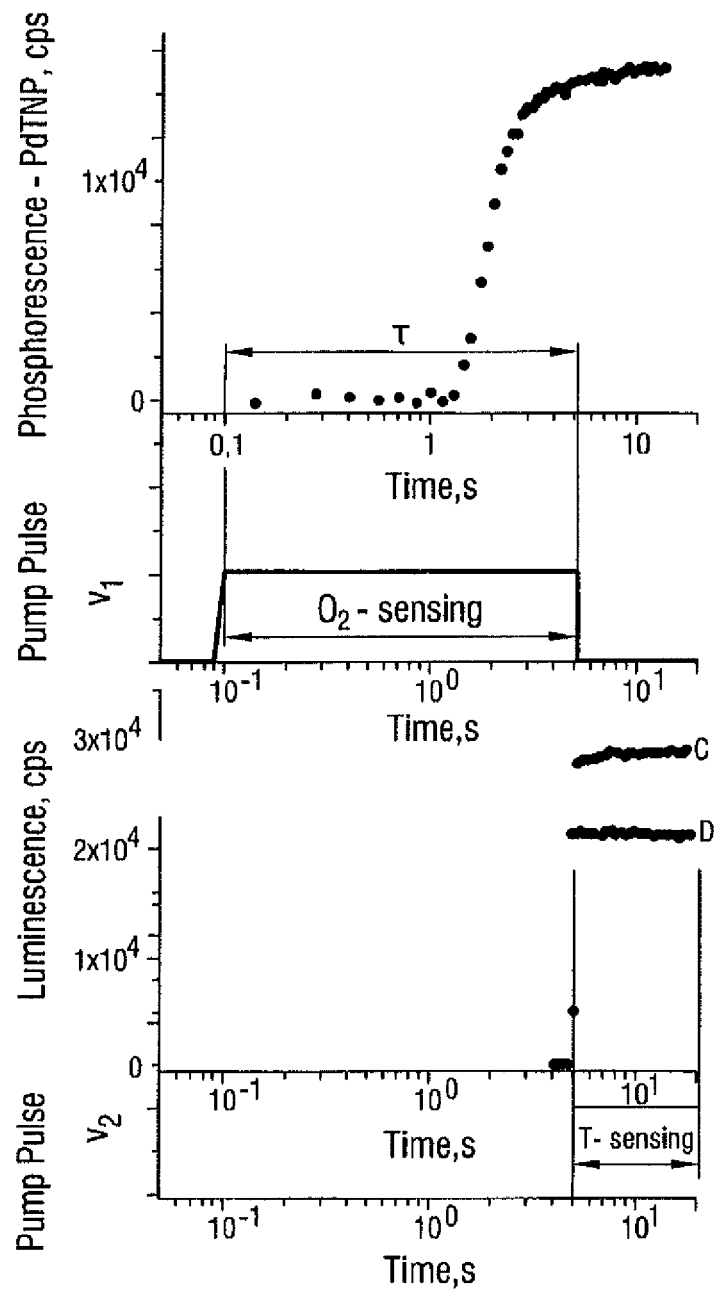

FIG. 3 shows the time sequence of the probing optical signals in the aforementioned nanocapsule including PdTNP/PdTBP/perylene/paraffin wax/di(5-hexen-1-yl) phenyl phosphate. The oxygen sensing was performed by using a diode laser with an emitting radiation at $\lambda=704$ nm (frequency $v_5$). Temperature sensing was done by excitation of another diode laser with radiation at $\lambda=635$ nm (frequency $v_2$). Phosphorescent signals ($v_1$ and $v_4$) as well the delayed fluorescent signals ($v_3$) were obtained by metal-packaged photomultipliers. The oxygen concentration was 50 ppm at the sample chamber. The sample temperature was −26° C. The time span shown in FIG. 3 for the oxygen sensing corresponds to the delay of phosphorescence for PdTNP (τ). Curve C shows the delayed emitter fluorescence ($v_3$) and curve D shows the residual sensitizer II (PdTBP) phosphorescence ($v_4$).

Figure 4:
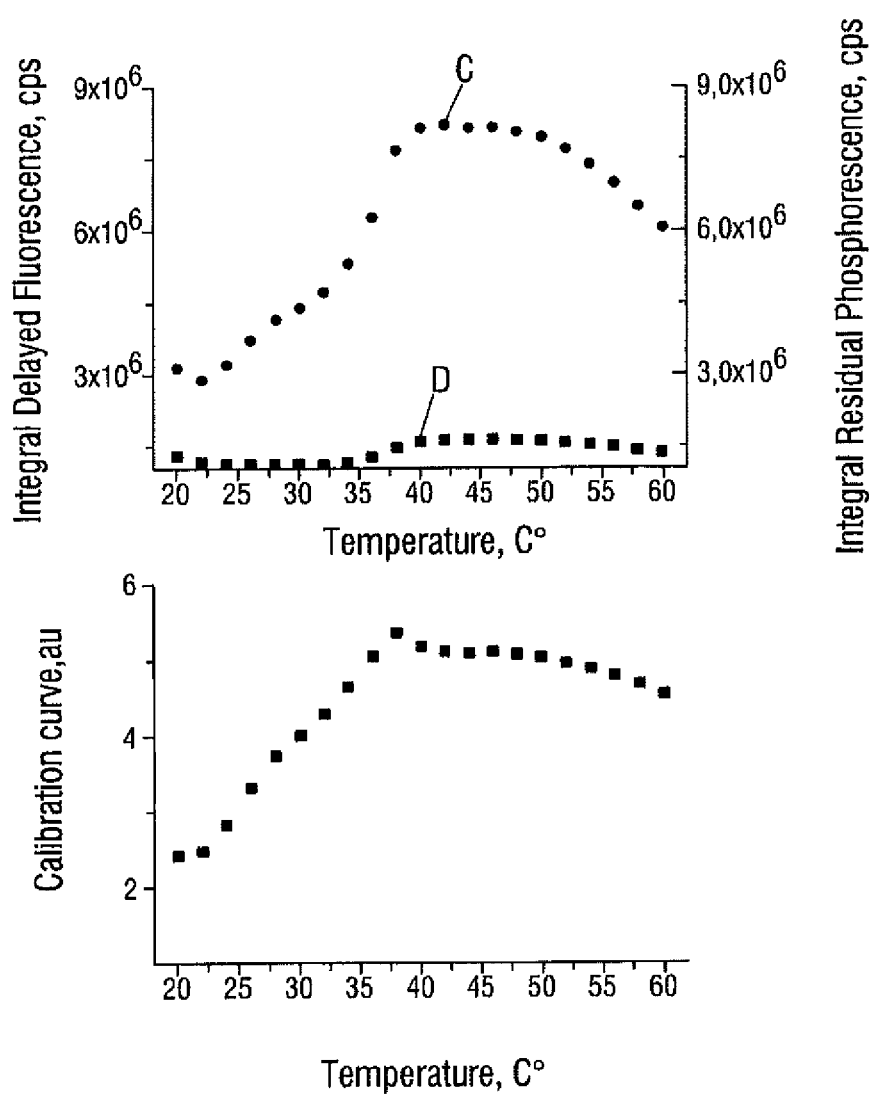

FIG. 4 shows in its top part integral optical signals, after procedure of optical scavenging of the present at the sensor molecular oxygen and the temperature dependence of the residual sensitizer II phosphorescence ($v_4$; curve D) and delayed emitter fluorescence ($v_3$; curve C). The bottom part shows the calibration curve and the ratiometric response in the aforementioned nano-encapsulated oxygen and temperature sensor including PdTNP/PdTBP/perylene/paraffin wax/ di(5-hexen-1-yl) phenyl phosphate and more specifically the ratio of delayed fluorescence and residual phosphorescence.

The invention claimed is:

1. A capsule, containing:
   i) at least one first sensitizer compound having a triplet state with a first triplet energy band and being capable of emitting light at a first frequency $v_1$ and being capable of energy transfer to triplet oxygen, wherein the at least one first sensitizer compound is selected from the group consisting of monoanthra[2,3]porphyrins, dianthra[2,3]porphyrins, trianthra[2,3]porphyrins, tetraanthra[2,3]porphyrins, mixed benzo- and naphtho-[2,3]porphyrins, mixed benzo- and anthra-[2,3]porphyrins, mixed naphtho- and anthra[2,3]porphyrins, and mixed benzo-, naphtho- and anthra-[2,3]porphyrins,
   ii) as matrix material at least one compound being capable of reacting with singlet oxygen, wherein the at least one compound capable of reacting with singlet oxygen comprises at least one terminal unsaturated carbon-carbon bond,
   iii) at least one second sensitizer compound having a triplet state with a second triplet energy band and being capable of absorbing radiation at a second frequency $v_2$ and of emitting light at a fourth frequency $v_4$, wherein the at least one second sensitizer compound is a compound according to any of the following general formulae (14) to (19):

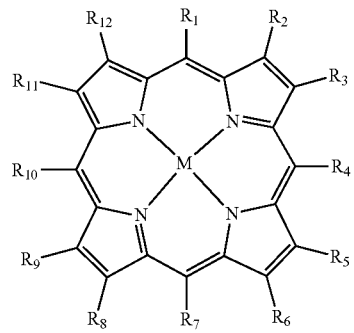

14

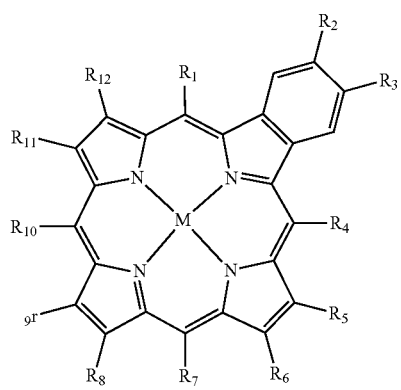

15

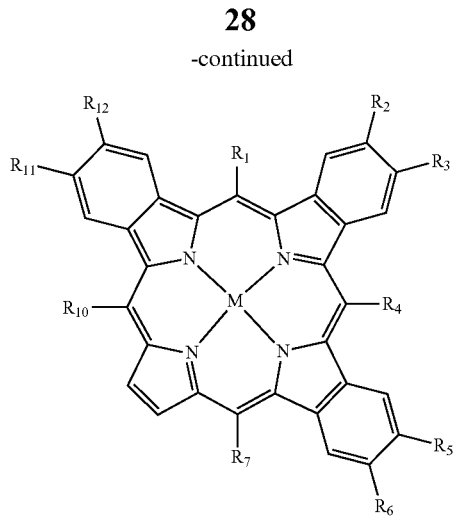

16

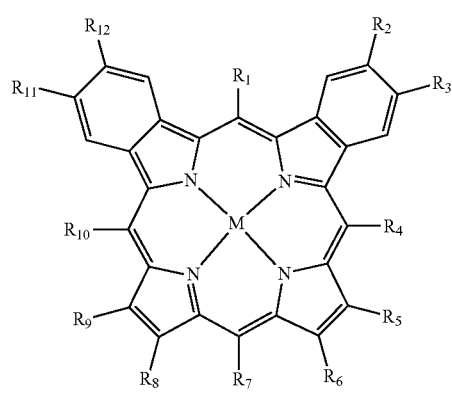

17

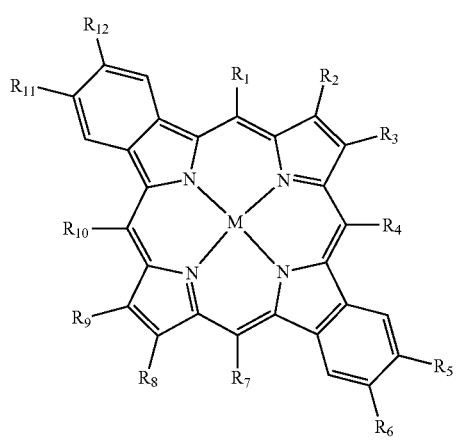

18

-continued

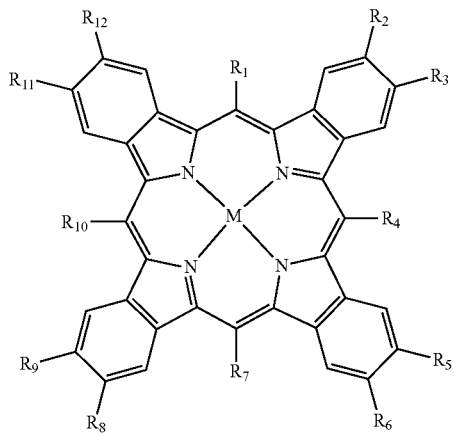

(19)

wherein in any of these formulae any of residues R1 to R12 is independently selected from the group consisting of hydrogen, alkyl, alkenyl, alkynyl, aryl, carboxy, alkoxy, alkylthio, aryloxy, arylthiol, alkoxycarbonyl, aryloxycarbonyl, alkylcarbonyl, arylcarbonyl, halogen, amino, alkylamino, arylamino, amide with alkyl and/or aryl groups, sulfonyl, alkylsulfonyl, and arylsulfonyl, wherein all of the aforementioned groups can carry additional linear or branched alkyl groups, negatively charged groups, positively charged groups, neutral water-solubilizing groups, and M is selected from the group consisting of zinc, copper, nickel, magnesium, iron, cadmium, tin, lead, palladium, platinum, ruthenium, rhenium, iridium, osmium, gold, bismuth, and uranium, iv) at least one emitter compound having a triplet state with a third triplet energy band, wherein the at least one second sensitizer compound is capable of transferring energy to the at least one emitter compound and wherein the at least one emitter compound, after obtaining energy transferred from the at least one second sensitizer compound, is capable of emitting light at a third frequency $v_3$, wherein the following equation is fulfilled: $v_3 > v_2$, wherein the at least one second sensitizer compound is capable of a triplet-triplet energy transfer to the at least one emitter compound and wherein the at least one emitter compound is capable of a triplet-triplet annihilation, wherein the least one emitter compound is a compound according to any of the following general formulae (20) to (24):

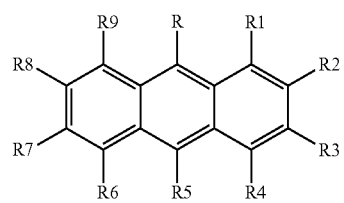

(20)

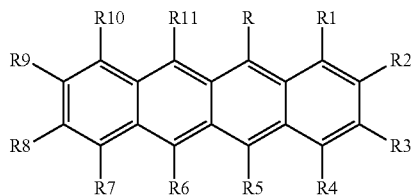

(21)

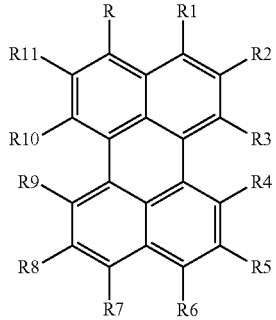

(22)

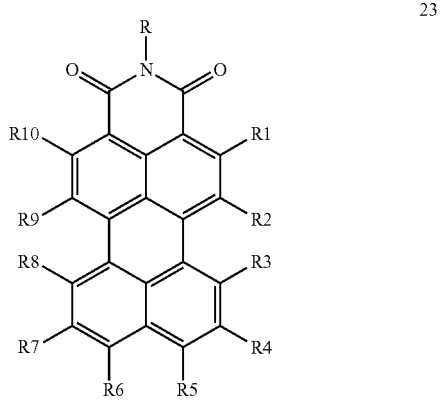

(23)

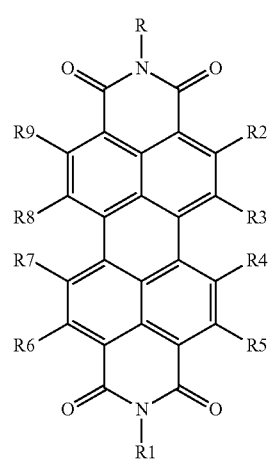

(24)

wherein in any of these formulae any of residues R, $R_1$ to $R_{12}$ is independently selected from the group consisting of hydrogen, alkyl, alkenyl, alkynyl, aryl, carboxy, alkoxy, alkylthio, aryloxy, arylthio, alkoxycarbonyl, aryloxycarbonyl, alkylcarbonyl, arylcarbonyl, halogen, amino, alkylamino, arylamino, amide with alkyl and/or aryl groups, sulfonyl, alkylsulfonyl and arylsulfonyl, wherein all of the aforementioned groups can carry additional linear or branched alkyl groups, negatively charged groups, positively charged groups, neutral water-solubilizing groups
wherein the upper energy limit of the first triplet energy band of the first sensitizer compound is lower than the lower energy limit of the second triplet energy band of the second sensitizer compound and lower than the lower energy limit of the third triplet energy band of the emitter compound, and wherein the third triplet band of the emitter compound at least partially overlaps with the second triplet energy band of the second sensitizer compound.

2. The capsule in accordance with claim 1, wherein the at least one first sensitizer compound is selected from the group consisting of monoanthra[2,3]porphyrins, dianthra[2,3]porphyrins, trianthra[2,3]porphyrins, tetraanthra[2,3]porphyrins and arbitrary combinations of two or more of the aforementioned compounds.

3. The capsule in accordance with claim 2, wherein the at least one first sensitizer compound is a compound according to any of the following general formulae (1) to (5):

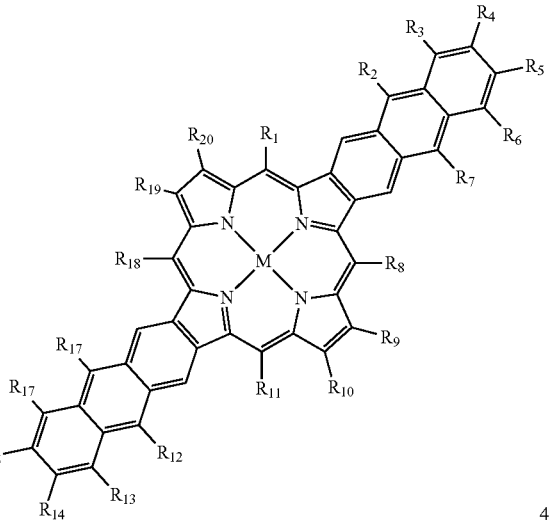

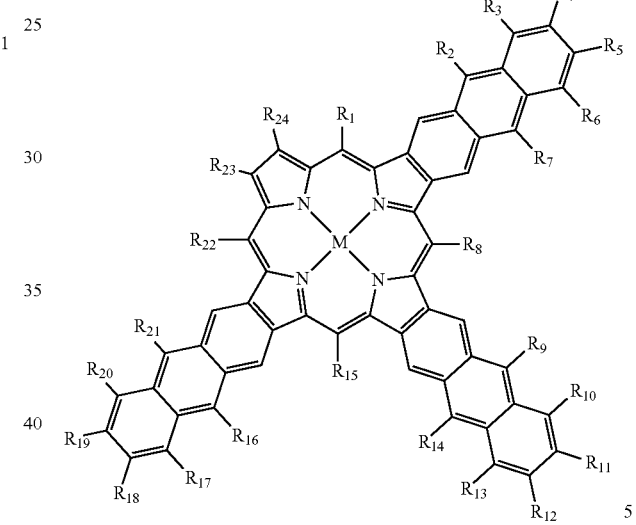

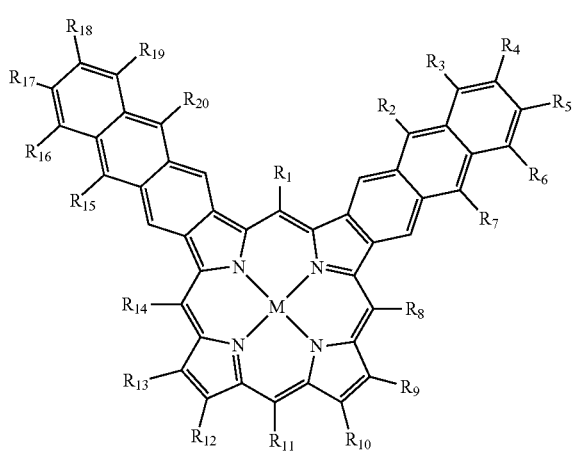

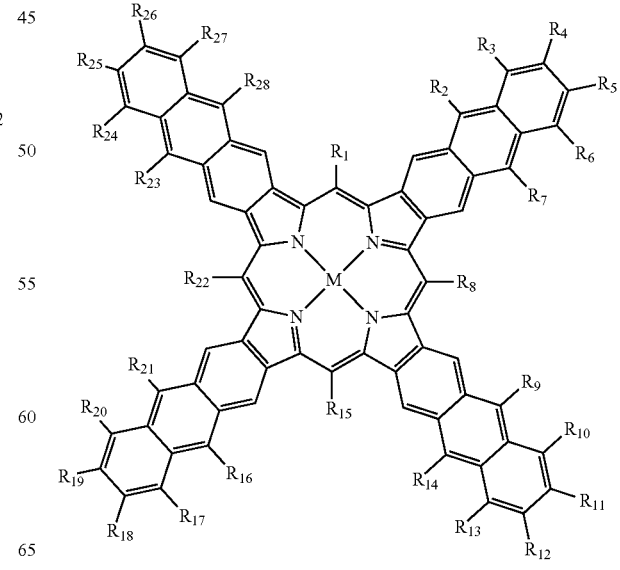

wherein
any of residues $R_1$ to $R_{28}$ is independently selected from the group of members consisting of hydrogen, alkyl, alkenyl, alkynyl, aryl, carboxy, alkoxy, alkylthio, aryloxy, arylthio, alkoxycarbonyl, aryloxycarbonyl, alkylcarbonyl, arylcarbonyl, halogen, amino, alkylamino, arylamino, amide with alkyl and/or aryl groups, sulfonyl, alkylsulfonyl and arylsulfonyl, wherein all of the aforementioned groups can carry additional linear or branched alkyl, positively charged groups, neutral water-solubilizing groups and M is selected from the group of members consisting of zinc, copper, nickel, magnesium, iron, cadmium, tin, lead, palladium, platinum, ruthenium, rhenium, iridium, osmium, gold, bismuth and uranium.

4. The capsule in accordance with claim 1, wherein the at least one first sensitizer compound is selected from the group of members consisting of mixed benzo- and naphtho-[2,3]porphyrins, mixed benzo- and anthra-[2,3]porphyrins, mixed naphtho- and anthra-[2,3]porphyrins, mixed benzo-, naphtho and anthra-[2,3]porphyrins and combinations off two or more of the aforementioned compounds.

5. The capsule in accordance with claim 1, wherein the at least one first sensitizer compound is a compound according to any of the following general formulae (6) to (13):

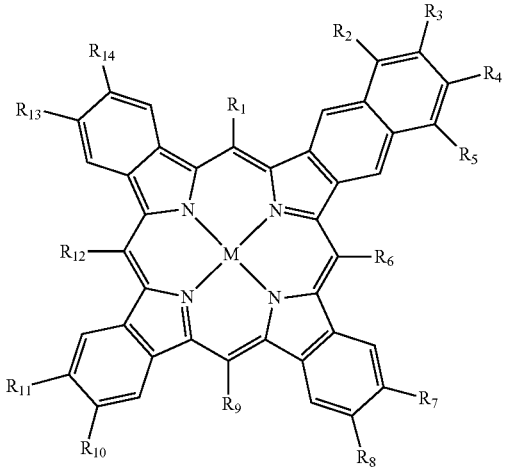

6

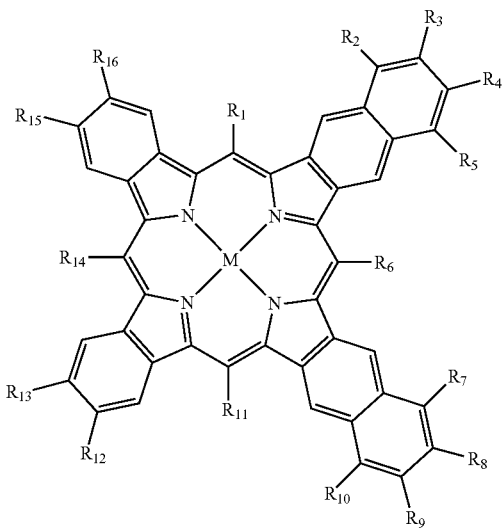

7

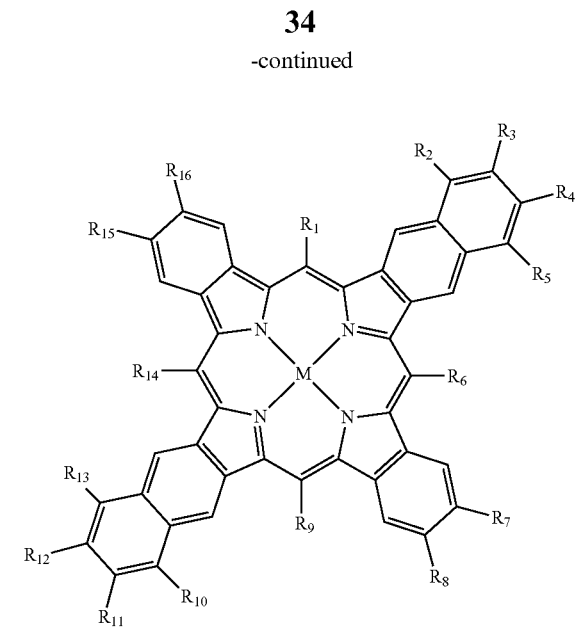

8

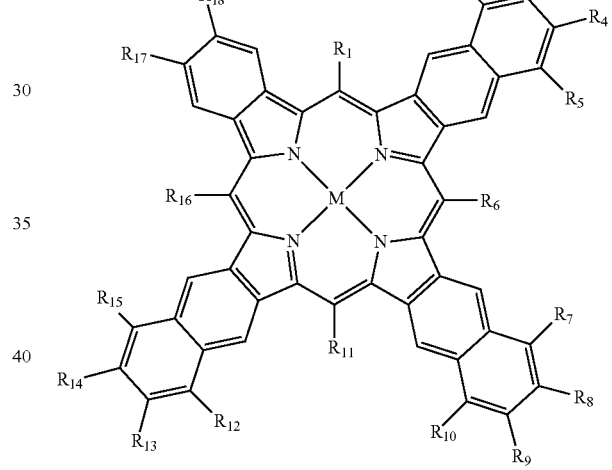

9

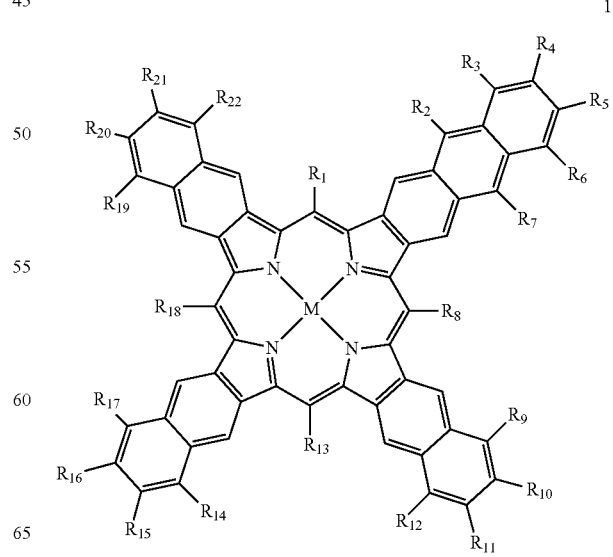

10

11

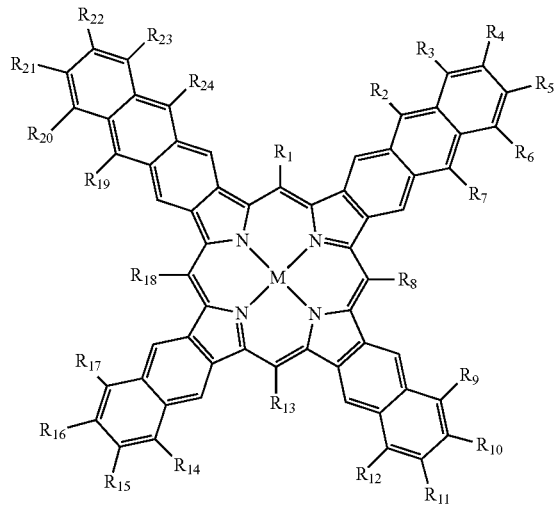

12

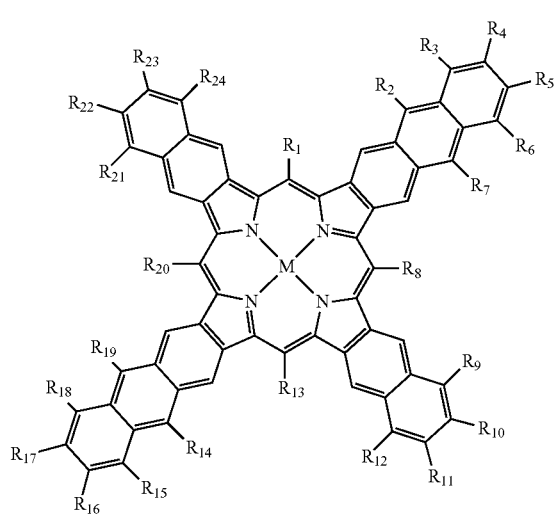

13

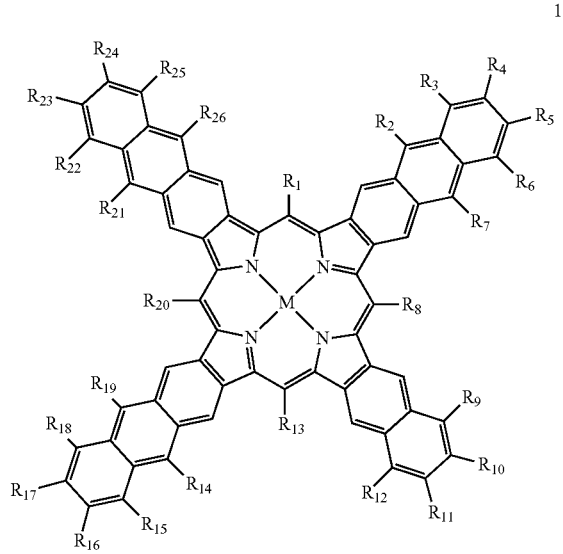

wherein any of residues $R_1$ to $R_{26}$ is independently selected from the group of members consisting of hydrogen, alkyl, alkenyl, alkynyl, aryl, carboxy, alkoxy, alkylthio, aryloxy, arylthio, alkoxycarbonyl, aryloxycarbonyl, alkylcarbonyl, arylcarbonyl, halogen, amino, alkylamino, arylamino, amide with alkyl and/or aryl groups, sulfonyl, alkylsulfonyl and arylsulfonyl, wherein all of the aforementioned groups can carry additional linear or branched alkyl groups, positively charged groups, neutral water-solubilizing groups and M is selected from the group of members consisting of zinc, copper, nickel, magnesium, iron, cadmium, tin, lead, palladium, platinum, ruthenium, rhenium, iridium, osmium, gold, bismuth and uranium.

6. The capsule in accordance with claim 1, wherein the concentration of the at least one first sensitizer compound in the capsule is $10^{-3}$ to $10^{-6}$ mol/l.

7. The capsule in accordance with claim 1, wherein the at least one compound being capable of reacting with singlet oxygen is selected from the group of members consisting of compounds having anyone of the following general formulae (I) to (X):

(I)

wherein

X is O or S,

R is alkenyl or alkynyl and

R1 is H, alkyl, ether-alkyl, ether-alkenyl, alkenyl, alkynyl, aralkyl, aryl or heteroaryl,

(II)

wherein

X is O or S,

R is alkenyl or alkynyl,

Y is alkyl, alkenyl, alkynyl, aralkyl, aralkenyl, aralkynyl, aryl or heteroaryl and R1, R2, R3 are independently from each other H, XR, alkyl, ether-alkyl, ether-alkenyl, alkenyl, alkynyl, aralkenyl, aralkynyl, aralkyl, aryl or heteroaryl, wherein X and R are as defined above,

(III)

wherein

X is N or P,

R is alkenyl or alkynyl and

R1 and R2 are independently from each other H, alkyl, alkenyl, alkynyl, aralkyl, aryl or heteroaryl,

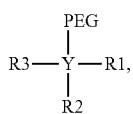  (IV)

wherein
PEG is an oligoethylene glycol or polyethylene glycol group having 2 to 99 ethylene glycol units,
R1 is alkenyl or alkynyl,
Y is Si and
R2 and R3 are independently from each other H, COOR, alkyl, alkenyl, alkynyl, aralkyl, aryl, heteroaryl or XR4, wherein X is N, P or As and R, R4 are independently from each other alkenyl or alkynyl,

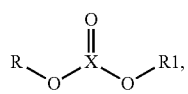  (V)

wherein
X is P, S, B or Si,
R is alkenyl or alkynyl and
R1 is H, alkyl, alkenyl, alkynyl, aralkyl, aryl or heteroaryl,

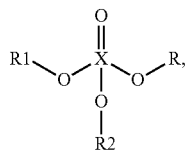  (VI)

wherein
X is P, S, B or Si,
R is alkenyl or alkynyl and
R1 and R2 are independently from each other H, alkyl, alkenyl, alkynyl, aralkyl, aryl or heteroaryl,

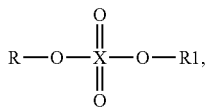  (VII)

wherein
X is P, S, B or Si,
R is alkenyl or alkynyl and
R1 is H, alkyl, alkenyl, alkynyl, aralkyl, aryl or heteroaryl,

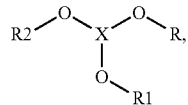  (VIII)

wherein
X is P, S, B or Si,
R is alkenyl or alkynyl and
R1 and R2 are independently from each other H, alkyl, alkenyl, alkynyl, aralkyl, aryl or heteroaryl,

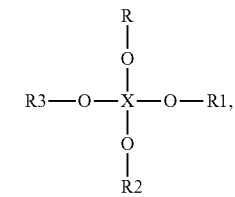  (IX)

wherein
X is P, S, B or Si,
R is alkenyl or alkynyl and
R1, R2 and R3 are independently from each other H, alkyl, alkenyl, alkynyl, aralkyl, aryl or heteroaryl,

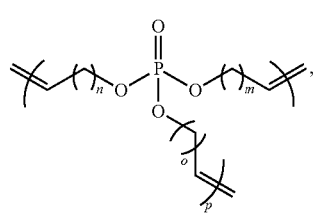  (Xa)

wherein
n, m and o are independently from each other an integer between 1 and 20 and
p is an integer of 2 or more,

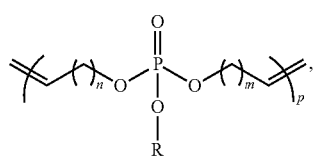  (Xb)

wherein
R is H, alkyl, alkenyl, alkynyl, aralkyl, aryl or heteroaryl,
n and m are independently from each other an integer between 1 and 20 and
p is an integer of 2 or more
or

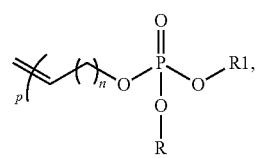  (Xc)

wherein
R and R1 are independently from each other H, alkyl, alkenyl, alkynyl, aralkyl, aryl or heteroaryl, n is an integer between 1 and 20 and p is an integer of 2 or more.

8. The capsule in accordance with claim 7, wherein the at least one compound capable of reacting with singlet oxygen is one according to the general formula (Xa), wherein n, m and o are independently from each other an integer between 1 and 10 and p is an integer of 2 to 120.

9. The capsule in accordance with claim 8, wherein the at least one compound capable of reacting with singlet oxygen is one according to the subsequent formulae (XI) to (XIV):

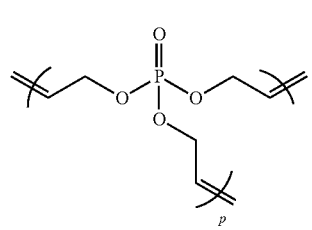

(XI)

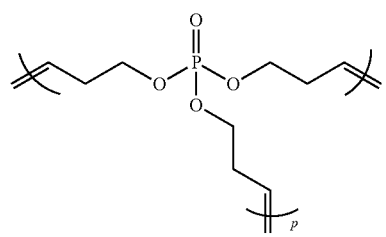

(XII)

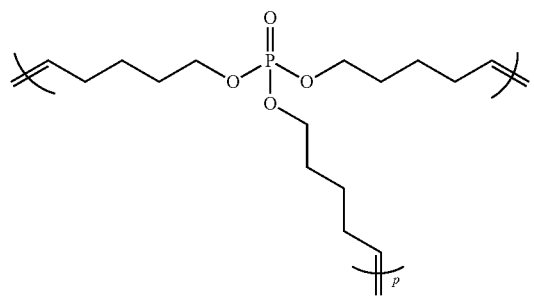

(XIII)

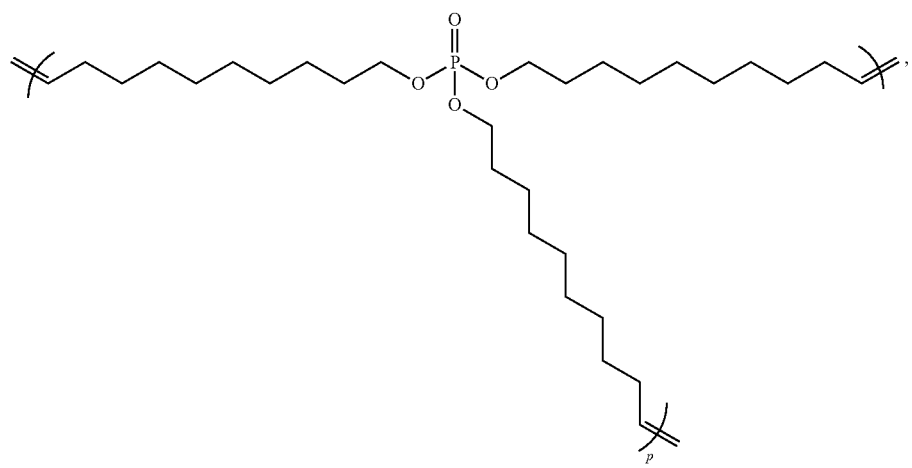

(XIV)

wherein in each of these formulae p is an integer of 2 to 120.

10. The capsule in accordance with claim 1, wherein the at least one compound capable of reacting with singlet oxygen is contained in the composition in such an amount that the number of terminal unsaturated carbon-carbon bonds of the at least one compound capable of reacting with singlet oxygen is at least 100 times higher in the composition than the number of molecules of all of the at least one first sensitizer compound.

11. The capsule in accordance with claim 1, wherein the concentration of the at least one emitter compound in the capsule is $2 \cdot 10^{-3}$ to $1 \cdot 10^{-6}$ mol/l.

12. The capsule in accordance with claim 1, wherein the capsule contains a further matrix material v).

13. The capsule in accordance with claim 12, wherein the further matrix material v) is selected from the group of members consisting of waxes, esters derived from a fatty acid and a fatty alcohol having one to four hydroxyl groups, triglycerides, glycol esters, polymers and mixtures of two or more of the aforementioned compounds.

14. The capsule in accordance with claim 1, wherein the capsule comprises a core including the components i) to iv), wherein the core is encapsulated by a shell.

15. The capsule in accordance with claim 14, wherein the shell is oxygen permeable.

16. The capsule in accordance with claim 14, wherein the core further includes the component v).

17. The capsule in accordance with claim 14, wherein the shell is composed of a polymer, of a metal oxide or of a hybrid material formed by a mixture of polymer and metal oxide.

18. A method of non-invasively determining the oxygen content and/or temperature in a living object comprising administering to the living object a capsule containing:

i) at least one first sensitizer compound having a triplet state with a first triplet energy band and being capable of emitting light at a first frequency $v_1$ and being capable of energy transfer to triplet oxygen, wherein the at least one first sensitizer compound is selected from the group consisting of monoanthra[2,3]porphyrins, dianthra[2,3]porphyrins, trianthra[2,3]porphyrins, tetraanthra[2,3]porphyrins, mixed benzo- and naphtho-[2,3]porphyrins, mixed benzo- and anthra-[2,3]porphyrins, mixed naphtho- and anthra[2,3]porphyrins, and mixed benzo-, naphtho- and anthra-[2,3]porphyrins, ii) as matrix material at least one compound being capable of reacting with singlet oxygen, wherein the at least one compound capable of reacting with singlet oxygen comprises at least one terminal unsaturated carbon-carbon bond, iii) at least one second sensitizer compound having a triplet state with a second triplet energy band and being capable of absorbing radiation at a second frequency $v_2$ and of emitting light at a fourth frequency $v_4$, wherein the at least one second sensitizer compound is a compound according to any of the following general formulae (14) to (19):

14
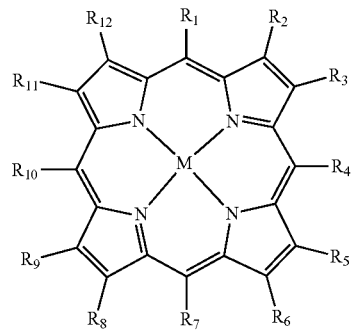

15
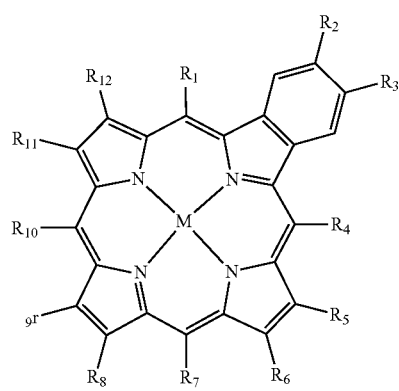

16
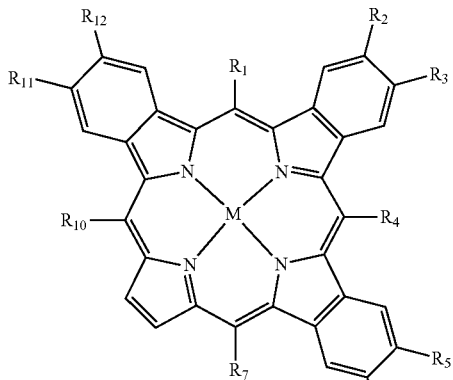

17

18
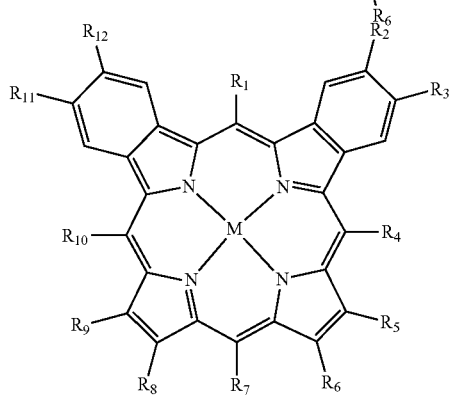

19
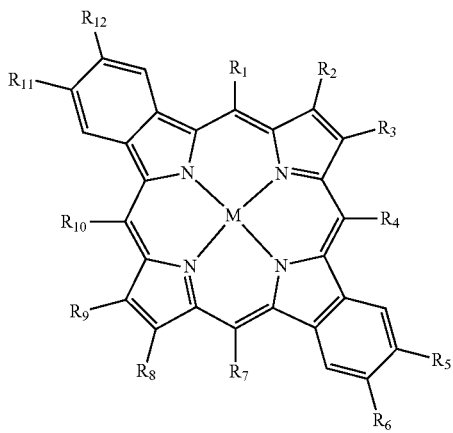

wherein in any of these formulae any of residues R1 to R12 is independently selected from the group consisting of hydrogen, alkyl, alkenyl, alkynyl, aryl, carboxy, alkoxy, alkylthio, aryloxy, arylthiol, alkoxycarbonyl, aryloxycarbonyl, alkylcarbonyl, arylcarbonyl, halogen, amino, alkylamino, arylamino, amide with alkyl and/or aryl groups, sulfonyl, alkylsulfonyl, and arylsulfonyl, wherein all of the aforementioned groups can carry additional linear or branched alkyl groups, negatively charged groups, positively charged groups, neutral water-solubilizing groups, and M is selected from the group consisting of zinc, copper, nickel, magnesium, iron, cadmium, tin, lead, palladium, platinum, ruthenium, rhenium, iridium, osmium, gold, bismuth, and uranium, iv) at least one emitter compound having a triplet state with a third triplet energy band, wherein the at least one second sensitizer compound is capable of transferring energy to the at least one emitter compound and wherein the at least one emitter compound, after obtaining energy transferred from the at least one second sensitizer compound, is capable of emitting light at a third frequency V3, wherein the following equation is fulfilled: V3>V2, wherein the at least one second sensitizer compound is capable of a triplet-triplet energy transfer to the at least one emitter compound and wherein the at least one emitter compound is capable of a triplet-triplet annihilation, wherein the least one emitter compound is a compound according to any of the following general formulae (201 to (24):

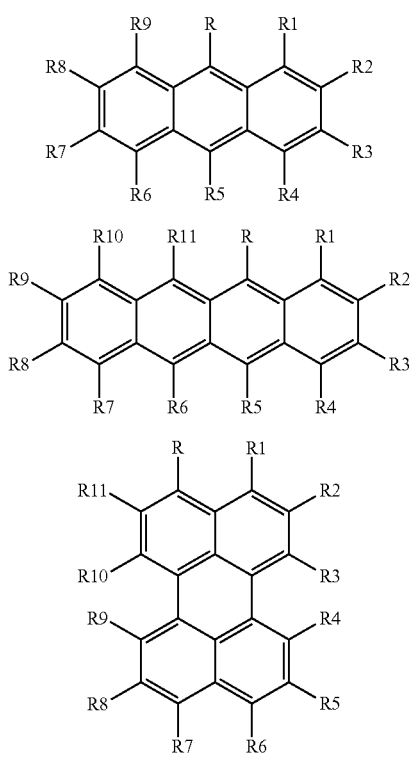

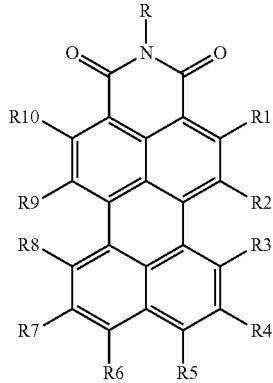

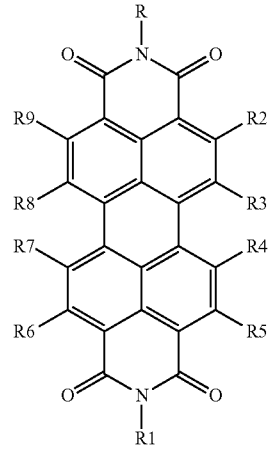

wherein
in any of these formulae any of residues R, Ri to R12 is independently selected from the group consisting of hydrogen, alkyl, alkenyl, alkynyl, aryl, carboxy, alkoxy, alkylthio, aryloxy, arylthio, alkoxycarbonyl, aryloxycarbonyl, alkylcarbonyl, arylcarbonyl, halogen, amino, alkylamino, arylamino, amide with alkyl and/or aryl groups, sulfonyl, alkylsulfonyl and arylsulfonyl, wherein all of the aforementioned groups can carry additional linear or branched alkyl groups, negatively charged groups, positively charged groups, neutral water-solubilizing groups wherein the upper energy limit of the first triplet energy band of the first sensitizer compound is lower than the lower energy limit of the second triplet energy band of the second sensitizer compound and lower than the lower energy limit of the third triplet energy band of the emitter compound, and wherein the third triplet band of the emitter compound at least partially overlaps with the second triplet energy band of the second sensitizer compound.

19. The method of claim 18 wherein oxygen content and temperature are simultaneously determined.

* * * * *